US012721804B2

(12) United States Patent
Fernandes

(10) Patent No.: US 12,721,804 B2
(45) Date of Patent: Sep. 1, 2026

(54) EMULSIFIED LIP GEL

(71) Applicant: L'OREAL, Paris (FR)

(72) Inventor: Sandrine Fernandes, Chevilly Larue (FR)

(73) Assignee: L'OREAL, Paris (FR)

( * ) Notice: Subject to any disclaimer, the term of this patent is extended or adjusted under 35 U.S.C. 154(b) by 570 days.

(21) Appl. No.: 17/788,172

(22) PCT Filed: Dec. 23, 2020

(86) PCT No.: PCT/EP2020/087814

§ 371 (c)(1),
(2) Date: Jun. 22, 2022

(87) PCT Pub. No.: WO2021/130335

PCT Pub. Date: Jul. 1, 2021

(65) Prior Publication Data

US 2023/0039503 A1 Feb. 9, 2023

(30) Foreign Application Priority Data

Dec. 23, 2019 (FR) ..................................... 19 15416

(51) Int. Cl.
*A61K 8/891* (2006.01)
*A61K 8/04* (2006.01)
*A61Q 1/06* (2006.01)

(52) U.S. Cl.
CPC .............. *A61K 8/891* (2013.01); *A61K 8/042* (2013.01); *A61Q 1/06* (2013.01); *A61K 2800/43* (2013.01); *A61K 2800/92* (2013.01)

(58) Field of Classification Search
None
See application file for complete search history.

(56) References Cited

U.S. PATENT DOCUMENTS 2,676,182 A 4/1954 Daudt et al.
3,627,851 A 12/1971 Brady
3,772,247 A 11/1973 Flannigan
4,935,484 A 6/1990 Wolfgruber et al.
5,082,706 A 1/1992 Tangney
5,110,890 A 5/1992 Butler
5,248,739 A 9/1993 Schmidt et al.
5,302,685 A 4/1994 Tsumura et al.
5,319,040 A 6/1994 Wengrovius et al.
5,538,793 A 7/1996 Inokuchi et al.
5,817,302 A 10/1998 Berthiaume et al.
11,311,465 B2 * 4/2022 Bouarfa .................. A61Q 1/02
2008/0299058 A1 12/2008 Saito et al.
2016/0000662 A1 * 1/2016 Ferrari .................. A61K 8/042
424/70.7
2017/0290747 A1 10/2017 Bouarfa et al.
2018/0036210 A1 * 2/2018 Dop ....................... A61K 8/345
2019/0133918 A1 * 5/2019 Scholler ................ A61K 8/898
2020/0113791 A1 4/2020 Manet et al.

FOREIGN PATENT DOCUMENTS

| | | | |
|---|---|---|---|
| EP | 0 242 219 | A2 | 10/1987 |
| EP | 0 285 886 | A1 | 10/1988 |
| EP | 0 295 886 | A2 | 12/1988 |
| EP | 0 765 656 | A1 | 4/1997 |
| EP | 1 086 683 | A1 | 3/2001 |
| EP | 0 815 928 | B1 | 5/2003 |
| FR | 853 634 | | 3/1940 |
| FR | 2 829 344 | A1 | 3/2003 |
| FR | 3 025 100 | A1 | 3/2016 |
| FR | 3 061 006 | A1 | 6/2018 |
| FR | 3 075 623 | A1 | 6/2019 |
| JP | 7-258460 | A | 10/1995 |
| JP | 9-188830 | A | 7/1997 |
| JP | 10-158450 | A | 6/1998 |
| JP | 10-158541 | A | 6/1998 |
| JP | 2017-502986 | A | 1/2017 |
| JP | 2019-532969 | A | 11/2019 |
| WO | WO 2005/075542 | A1 | 8/2005 |
| WO | WO 2008/155059 | A2 | 12/2008 |
| WO | WO 2015/108950 | A1 | 7/2015 |
| WO | WO 2018/081762 | A2 | 5/2018 |

OTHER PUBLICATIONS

DOWSIL 593 fluid.*
Belsil PDM 1000 wayback machine Oct. 7, 2017.*
Japanese Office Action issued Aug. 29, 2023 in Japanese Application 2022-538481, (with English translation), 16 pages.
Mintel GNPD, "$_2$ in 1 Lip & Cheek Chiffon Tint", URL: https portal.mintel.com [retrieved on Aug. 16, 2023], Jul. 2019, 4 pages.
International Search Report issued Feb. 9, 2021 in PCT/EP2020/087814, filed on Dec. 23, 2020, 4 pages.
Anonymous "Xiameter ™ PMX-200 Silicone Fluid 5 cSt", Safety Data Sheet, XP055730206, Jun. 12, 2019, 10 pages.
Delvalle et al. "Personal Care Applications for Phenylsilsesquioxane Resins", IP.com, XP013173823, Dec. 22, 2016, 18 pages.
Anonymous "Crème Rich Moisturising Care", Database GNPD [online] Mintel, XP055584361, Dec. 19, 2016, 8 pages.
Postiaux et al. "Silicone acrylate copolymers in lipstick and color cosmetics", Research Disclosure, Kenneth Mason Publications, vol. 495, No. 5, Jul. 5, 2005, 4 pages.
"Selecting the perfect silicone for your Formulation" Personal Care, XP002800305, Jul. 9, 2014, 4 pages.

* cited by examiner

*Primary Examiner* — Danah Al-Awadi
(74) *Attorney, Agent, or Firm* — Oblon, McClelland, Maier & Neustadt, L.L.P.

(57) ABSTRACT

The present invention relates to a composition, especially a cosmetic composition, in particular for making up and/or caring for keratin materials, comprising at least one aqueous phase containing at least one non-particulate synthetic polymeric gelling agent, and one oily phase containing at least one silicone elastomer, one silicone resin, and one non-volatile silicone oil comprising at least one dimethicone group, or one non-volatile ester oil, or mixtures thereof.

19 Claims, No Drawings

EMULSIFIED LIP GEL

TECHNICAL FIELD

The present invention is directed toward proposing for the field of caring for and/or making up keratin materials, especially the skin and/or the lips, and in particular the lips, novel compositions that are very particularly advantageous with regard to the technical performance and the sensations they afford the user during their application to said keratin materials, in particular to the lips.

PRIOR ART

In general, cosmetic compositions need to afford an esthetic effect when applied to the skin and/or the lips, and to maintain this esthetic effect over time.

The production of an esthetic effect, after applying a cosmetic composition, results from a set of properties intrinsic to the composition which are expressed in terms of makeup performance, cosmetic properties such as comfort on application, ease of application, smoothness on application and on wearing, freshness, no feeling of tautness, homogeneity, lightness and a satisfactory finish of the deposit made with the composition.

In particular, producing a liquid composition which is homogeneous and stable over time, and the deposit of which on the skin or lips is homogeneous, fresh and light with a satisfactory finish without developing tackiness, is an ongoing concern of formulators working in the field of lipsticks, and other skincare and/or lipcare products.

More particularly, in the liquid lipstick market, there are two categories of products, namely matte products and gloss products.

Within these categories, compositions delivering a thin film and a matte finish have the drawbacks of lacking comfort on the lips, and of drying them out.

The compositions delivering a thin glossy film are judged for their part to be more comfortable. However, the deposits made with such compositions generally do not have the degree of color intensity of products delivering a thin matte film. Furthermore, unlike matte products, these deposits migrate and are generally tacky.

Thus, the development of formulations dedicated to making up and/or caring for the lips, possessing the advantageous properties of matte products and of gloss products, namely delivering a thin film endowed with satisfactory properties, in particular in terms of application, comfort, wear property and coverage, hydration but also in terms of makeup effects, is an ongoing objective.

Furthermore, the compositions must also make it possible to limit the migration of the composition into the wrinkles and fine lines of the lip contour after application and to have limited color transfer and tackiness, without a feeling of tautness or dryness once they are applied.

DISCLOSURE OF THE INVENTION

The objective of the present invention is therefore to introduce a new category in the liquid lipsticks market having the advantages of the two existing categories, namely matte products and gloss products, in a single product.

There therefore remains the need to have stable cosmetic compositions capable of forming a thin, homogeneous and satiny deposit on the skin and/or the lips, and having comfort, wear property and freshness properties, which transfer little or not at all, and which are not very tacky or not at all tacky, and are non-migrating, while having a good color intensity.

The object of the present invention is, precisely, to meet these needs.

SUMMARY OF THE INVENTION

Thus, according to one of its aspects, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) one silicone resin; and (iii) one non-volatile silicone oil comprising at least one dimethicone group, or one non-volatile ester oil, or mixtures thereof.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) one silicone resin; and (iii) one non-volatile silicone oil comprising at least one dimethicone group, and preferably chosen from non-volatile phenyl silicone oils comprising at least one dimethicone group, optionally in mixture with a non-volatile ester oil.

Against all expectations, the inventors have observed that the compositions according to the invention advantageously have very good sensory performance and have an excellent makeup result.

In particular, as emerges from the examples appearing below, the compositions according to the invention are comfortable on application and over time. They deliver a thin film, and are not, or not very, tacky.

Moreover, they are stable, do not migrate, and transfer little or not at all. Advantageously, they have good coverage, good color intensity and have a satiny finish.

DETAILED DESCRIPTION

Non-Particulate Synthetic Polymeric Gelling Agent

As indicated above, a composition according to the invention comprises in its aqueous phase at least one non-particulate synthetic polymeric gelling agent.

For the purposes of the invention, the term "synthetic" means that the polymer is neither naturally existing nor a derivative of a polymer of natural origin.

For the purposes of the invention, the term "non-particulate" means that the polymer is not in the form of particles, for example spherical particles.

It is understood that the non-particulate synthetic polymeric gelling agent is not a film-forming latex.

As emerges from what follows, the non-particulate synthetic polymeric gelling agent is in particular chosen from associative polymers, in particular associative polymers of polyurethane type, polyacrylamides, crosslinked and/or neutralized 2-acrylamido-2-methylpropanesulfonic acid polymers and copolymers, modified or unmodified carboxyvinyl polymers, and mixtures thereof, notably as defined below.

A composition according to the invention may comprise from 0.1% to 6% by weight, in particular from 0.5% to 5.5% by weight, and preferably from 1% to 5% by weight of non-particulate synthetic polymeric gelling agent(s), relative to the total weight of the composition.

Associative Polymers

For the purposes of the present invention, the term "associative polymer" means any amphiphilic polymer including in its structure at least one fatty chain and at least one hydrophilic portion. The associative polymers in accordance with the present invention may be anionic, cationic, nonionic or amphoteric.

Among the associative anionic polymers, mention may be made of those comprising at least one hydrophilic unit, and at least one fatty-chain allyl ether unit. Among the associative anionic polymers, mention may also be made of maleic anhydride/$C_{30}$-$C_{38}$-α-olefin/alkyl maleate terpolymers, such as the maleic anhydride/$C_{30}$-$C_{38}$-α-olefin/isopropyl maleate copolymer product sold under the name Performa V 1608® by the company Newphase Technologies. Among the associative anionic polymers, mention may be made, according to a preferred embodiment, of copolymers comprising among their monomers an α,β-monoethylenically unsaturated carboxylic acid and an ester of an α,β-monoethylenically unsaturated carboxylic acid and of an oxyalkylenated fatty alcohol. As associative anionic polymers, mention may also be made of anionic polymers comprising at least one hydrophilic unit of olefinic unsaturated carboxylic acid type, and at least one hydrophobic unit exclusively of ($C_{10}$-$C_{30}$) alkyl ester of unsaturated carboxylic acid type. As associative anionic polymers, mention may also be made of anionic terpolymers.

As cationic associative polymers, mention may be made of polyacrylates containing amine side groups, such as the 8781-121B® or 9492-103® polymers from the company National Starch.

The nonionic associative polymers may be chosen from copolymers of vinylpyrrolidone and of fatty-chain hydrophobic monomers, copolymers of $C_1$-$C_6$ alkyl acrylates or methacrylates and of amphiphilic monomers comprising at least one fatty chain, copolymers of hydrophilic acrylates or methacrylates and of hydrophobic monomers comprising at least one fatty chain, such as polyethylene glycol methacrylate/lauryl methacrylate copolymer, associative polyurethanes, such as polyether polyurethanes, for example fatty-chain nonionic polyether polyurethanes.

Among the associative amphoteric polymers, mention may be made of crosslinked or non-crosslinked, branched or unbranched amphoteric polymers, such as acrylic acid/acrylamidopropyltrimethylammonium chloride/stearyl methacrylate copolymers. According to a preferred embodiment, the associative polymer is chosen from nonionic associative polymers and more particularly from associative polyurethanes, such as Steareth-100/PEG-136/HDI Copolymer sold under the name Rheolate FX 1100® by Elementis.

Polyacrylamides and 2-Acrylamido-2-Methylpropanesulfonic Acid Polymers and Copolymers The polymers used that are suitable as gelling agent for the invention may be crosslinked or non-crosslinked homopolymers or copolymers comprising at least the 2-acrylamido-2-methylpropanesulfonic acid (AMPS®) monomer, in a form partially or totally neutralized with a mineral base other than aqueous ammonia, such as sodium hydroxide or potassium hydroxide.

They are preferably totally neutralized or almost totally neutralized, i.e. at least 90% neutralized.

These AMPS® polymers according to the invention may be crosslinked or non-crosslinked. When the polymers are crosslinked, the crosslinking agents may be chosen from the polyolefinically unsaturated compounds commonly used for crosslinking polymers obtained by radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol di(meth)acrylate, tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allyl ethers of alcohols of the sugar series, or other allyl or vinyl ethers of polyfunctional alcohols, and also allyl esters of phosphoric and/or vinylphosphonic acid derivatives, or mixtures of these compounds.

According to a preferred embodiment of the invention, the crosslinking agent is chosen from methylenebisacrylamide, allyl methacrylate and trimethylolpropane triacrylate (TMPTA).

The degree of crosslinking generally ranges from 0.01 mol % to 10 mol % and more particularly from 0.2 mol % to 2 mol % relative to the polymer.

The AMPS® polymers that are suitable for use in the invention are water-soluble or water-dispersible. In this case, they are either "homopolymers" comprising only AMPS® monomers and, if they are crosslinked, one or more crosslinking agents such as those defined above, or copolymers obtained from AMPS® and one or more hydrophilic or hydrophobic ethylenically unsaturated monomers and, if they are crosslinked, one or more crosslinking agents such as those defined above. When said copolymers include hydrophobic ethylenically unsaturated monomers, these monomers do not include a fatty chain and are preferably present in small amounts.

For the purpose of the present invention, the term "fatty chain" means any hydrocarbon-based chain including at least 7 carbon atoms.

The term "water-soluble or water-dispersible" means polymers which, when introduced into an aqueous phase at 25° C., at a mass concentration equal to 1%, make it possible to obtain a macroscopically homogeneous and transparent solution, i.e. a solution with a maximum light transmittance value, at a wavelength equal to 500 nm, through a sample 1 cm thick, of at least 60%, preferably of at least 70%.

The "homopolymers" according to the invention are preferably crosslinked and neutralized, and they may be obtained according to the preparation process comprising the following steps: (a) the monomer such as AMPS® is dispersed or dissolved in free form in a solution of tert-butanol or of water and tert-butanol; (b) the monomer solution or dispersion obtained in (a) is neutralized with one or more mineral or organic bases, preferably aqueous ammonia $NH_3$, in an amount making it possible to obtain a degree of neutralization of the sulfonic acid functions of the polymer ranging from 90% to 100%; (c) the crosslinking monomer(s) are added to the solution or dispersion obtained in (b); (d) a standard free-radical polymerization is performed in the presence of free-radical initiators at a temperature ranging from 10° C. to 150° C.; the polymer precipitating in the tert-butanol-based solution or dispersion.

The water-soluble or water-dispersible AMPS® copolymers according to the invention contain water-soluble ethylenically unsaturated monomers, hydrophobic monomers, or mixtures thereof.

The water-soluble comonomers may be ionic or nonionic.

Among the ionic water-soluble comonomers, mention may for example be made of the following compounds and salts thereof: (meth)acrylic acid, styrenesulfonic acid, vinylsulfonic acid and (meth)allylsulfonic acid, vinylphosphonic acid, maleic acid, itaconic acid, crotonic acid, water-soluble vinyl monomers of formula (A) below:

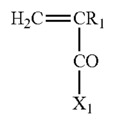

(A)

wherein $R_1$ is chosen from —H, —$CH_3$, —$C_2H_5$ or —$C_3H_7$; $X_1$ is chosen from alkyl oxides of —$OR_2$ type where $R_2$ is a linear or branched, saturated or unsaturated hydrocarbon-based radical having from 1 to 6 carbon atoms, substituted with at least one sulfonic (—$SO^{3-}$) and/or sulfate (—$SO^{4-}$) and/or phosphate (—$PO_4H_2^-$) group.

Among the nonionic water-soluble comonomers, mention may for example be made of (meth)acrylamide, N-vinylacetamide and N-methyl N-vinylacetamide, N-vinylformamide and N-methyl N-vinylformamide, maleic anhydride, vinylamine, N-vinyllactams comprising a cyclic alkyl group having from 4 to 9 carbon atoms, such as N-vinylpyrrolidone, N-butyrolactam and N-vinylcaprolactam, vinyl alcohol of formula $CH_2$=CHOH, the water-soluble vinyl monomers of formula (B) below:

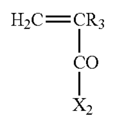

(B)

wherein $R_3$ is chosen from —H, —$CH_3$, —$C_2H_5$ or —$C_3H_7$; $X_2$ is chosen from alkyl oxides of —$OR_4$ type where $R_4$ is a linear or branched, saturated or unsaturated hydrocarbon-based radical having from 1 to 6 carbon atoms, optionally substituted with a halogen atom (iodine, bromine, chlorine, fluorine); a hydroxyl (—OH) group; ether.

Mention is made, for example, of glycidyl (meth)acrylate, hydroxyethyl methacrylate, and (meth)acrylates of ethylene glycol, of diethylene glycol or of polyalkylene glycol.

Among the hydrophobic comonomers without a fatty chain, mention may be made, for example, of styrene and derivatives thereof, such as 4-butylstyrene, α-methylstyrene and vinyltoluene; vinyl acetate of formula $CH_2$=CH—$OCOCH_3$; vinyl ethers of formula $CH_2$=CHOR wherein R is a linear or branched, saturated or unsaturated hydrocarbon-based radical having from 1 to 6 carbon atoms; acrylonitrile; caprolactone; vinyl chloride and vinylidene chloride; silicone derivatives, which, after polymerization, result in silicone polymers such as methacryloxypropyltris(trimethylsiloxy)silane and silicone methacrylamides; hydrophobic vinyl monomers of formula (C) below:

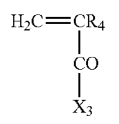

(C)

wherein $R_4$ is chosen from —H, —$CH_3$, —$C_2H_5$ or —$C_3H_7$; $X_3$ is chosen from alkyl oxides of —$OR_5$ type where $R_5$ is a linear or branched, saturated or unsaturated hydrocarbon-based radical having from 1 to 6 carbon atoms.

Mention is made, for example, of methyl methacrylate, ethyl methacrylate, n-butyl (meth)acrylate, tert-butyl (meth) acrylate, cyclohexyl acrylate and isobornyl acrylate and 2-ethylhexyl acrylate.

The water-soluble or water-dispersible AMPS® polymers of the invention preferably have a molar mass ranging from 50 000 g/mol to 10 000 000 g/mol, preferably from 80 000 g/mol to 8 000 000 g/mol, and even more preferably from 10 000 g/mol to 7 000 000 g/mol. As water-soluble or water-dispersible AMPS® homopolymers suitable for use in the invention, mention may be made, for example, of crosslinked or non-crosslinked polymers of sodium acrylamido-2-methylpropanesulfonate, such as that used in the commercial product Simulgel 800® (CTFA name: Sodium Polyacryloyldimethyl Taurate), crosslinked ammonium acrylamido-2-methylpropanesulfonate polymers (INCI name: Ammonium Polyacryldimethyltauramide) such as those described in patent EP 0 815 928 B1 and such as the product sold under the trade name Hostacerin AMPS® by the company Clariant. Preferably, a composition according to the invention comprises an AMPS® homopolymer. As water-soluble or water-dispersible AMPS® copolymers in accordance with the invention, examples that may be mentioned include:

- crosslinked acrylamide/sodium acrylamido-2-methylpropanesulfonate copolymers, such as that used in the commercial product Sepigel 305® (CTFA name: Polyacrylamide/$C_{13}$-$C_{14}$ Isoparaffin/Laureth-7) or that used in the commercial product sold under the name Simulgel 600® (CTFA name: Acrylamide/Sodium acryloyldimethyltaurate/Isohexadecane/Polysorbate-80) by the company SEPPIC;
- copolymers of AMPS® and of vinylpyrrolidone or vinylformamide, such as that used in the commercial product sold under the name Aristoflex AVC® by the company Clariant (CTFA name: Ammonium Acryloyldimethyltaurate/VP Copolymer) but neutralized with sodium hydroxide or potassium hydroxide;
- copolymers of AMPS® and of sodium acrylate, for instance the AMPS®/sodium acrylate copolymer, such as that used in the commercial product sold under the name Simulgel EG® by the company SEPPIC or under the trade name Sepinov EM® (CTFA name: Hydroxyethyl Acrylate/Sodium Acryloyldimethyltaurate copolymer);
- copolymers of AMPS® and of hydroxyethyl acrylate, for instance the AMPS®/hydroxyethyl acrylate copolymer, such as that used in the commercial product sold under the name Simulgel NS® by the company SEPPIC (CTFA name: Hydroxyethyl Acrylate/Sodium Acryloyldimethyltaurate copolymer (And) Squalane (And) Polysorbate 60), or such as the product sold under the name Sodium acrylamido-2-methylpropanesulfonate/hydroxyethyl acrylate copolymer, such as the commercial product Sepinov EMT 10® (INCI name: Hydroxyethyl Acrylate/Sodium Acryloyldimethyltaurate copolymer).

As preferred water-soluble or water-dispersible AMPS® copolymers in accordance with the invention, mention may be made of copolymers of AMPS® and of hydroxyethyl acrylate.

Modified or Unmodified Carboxyvinyl Polymers

The modified or unmodified carboxyvinyl polymers may be copolymers derived from the polymerization of at least one monomer (a) chosen from α,β-ethylenically unsaturated carboxylic acids or esters thereof, with at least one ethylenically unsaturated monomer (b) including a hydrophobic group. The term "copolymers" means both copolymers obtained from two types of monomer and those obtained from more than two types of monomer, such as terpolymers obtained from three types of monomer. According to a preferred embodiment, these polymers are crosslinked.

Among these polymers, the ones that are preferred according to the present invention are acrylate/$C_{10}$-$C_{30}$-alkyl acrylate copolymers (INCI name: Acrylates/$C_{10-30}$ Alkyl acrylate Crosspolymer) such as the products sold by the company Lubrizol under the trade names Pemulen TR-1®, Pemulen TR-2®, Carbopol 1382®, Carbopol EDT 2020® and Carbopol Ultrez 20 Polymer®, and more preferentially still Pemulen TR-2®.

Among the modified or unmodified carboxyvinyl polymers, mention may also be made of sodium polyacrylates, such as those sold under the name Cosmedia SP® or Cosmedia SPL®, sold by the company Cognis.

Mention may also be made of partially neutralized sodium polyacrylates that are in the form of a reverse emulsion comprising at least one polar oil, for example the product sold under the name Luvigel® EM by the company BASF.

The modified or unmodified carboxyvinyl polymers may also be chosen from crosslinked (meth)acrylic acid homopolymers. For the purposes of the present patent application, the term "(meth)acrylic" means "acrylic or methacrylic". Examples that may be mentioned include the products sold by Lubrizol under the names Carbopol® 910, 934, 940, 941, 934 P, 980, 981, 2984, 5984 and Carbopol® Ultrez 10 Polymer, or by 3V-Sigma under the name Synthalen® K, Synthalen® L or Synthalen® M.

Among the modified or unmodified carboxyvinyl polymers, mention may be made in particular of Carbopol® (CTFA name: carbomer) and Pemulen® (CTFA name: Acrylates/$C_{10-30}$ alkyl acrylate crosspolymer), sold by the company Lubrizol.

Preferably, a composition according to the invention comprises a non-particulate synthetic polymeric hydrophilic gelling agent chosen from 2-acrylamido-2-methylpropanesulfonic acid polymers and copolymers.

According to a specific variant, the non-particulate synthetic polymeric hydrophilic gelling agent is an AMPS® homopolymer.

According to a preferred variant, the non-particulate synthetic polymeric hydrophilic gelling agent is a a copolymer of 2-acrylamido-2-methylpropanesulfonic acid, and more preferentially a copolymer of 2-acrylamido-2-methylpropanesulfonic acid and of hydroxyethyl acrylate.

Silicone Elastomer

The silicone elastomer is present in the oily phase of the composition.

The term "silicone elastomer" or "organopolysiloxane elastomer" means a supple, deformable organopolysiloxane with viscoelastic properties and notably with the consistency of a sponge or a supple sphere. Its modulus of elasticity is such that this material withstands deformation and has limited stretchability and contractibility. This material is capable of regaining its original shape after stretching. It is understood that a silicon elastomer is different from a surfactant, and notably from a silicon surfactant.

It may more particularly be a crosslinked silicone elastomer. Preferably, the silicone elastomer is not highly crosslinked.

Thus, the silicone elastomer may be obtained by crosslinking addition reaction of diorganopolysiloxane containing at least one hydrogen bonded to silicon and of diorganopolysiloxane containing ethylenically unsaturated groups bonded to silicon, or else of hydrocarbon-based chain having ethylenically unsaturated groups at each end, notably in the presence of a platinum catalyst; or by dehydrogenation crosslinking condensation reaction between a hydroxyl-terminated diorganopolysiloxane and a diorganopolysiloxane containing at least one hydrogen bonded to silicon, notably in the presence of an organotin; or by crosslinking condensation reaction of a hydroxyl-terminated diorganopolysiloxane and of a hydrolyzable organopolysilane; or by thermal crosslinking of organopolysiloxane, notably in the presence of an organoperoxide catalyst; or by crosslinking of organopolysiloxane via high-energy radiation such as gamma rays, ultraviolet rays or an electron beam.

Preferably, the silicone elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, notably in the presence (C) of a platinum catalyst, as described, for instance, in patent application EP 295 886.

In particular, the silicone elastomer may be obtained by reaction of dimethylvinylsiloxy-terminated dimethylpolysiloxane and of trimethylsiloxy-terminated methylhydropolysiloxane, in the presence of a platinum catalyst.

Compound (A) is the base reagent for the formation of silicone elastomer, and the crosslinking is performed by addition reaction of compound (A) with compound (B) in the presence of catalyst (C).

Compound (A) is in particular an organopolysiloxane containing at least two hydrogen atoms bonded to different silicon atoms in each molecule.

Compound (A) may have any molecular structure, notably a linear-chain or branched-chain structure or a cyclic structure.

Compound (A) may have a viscosity at 25° C. ranging from 1 to 50 000 centistokes, notably so as to be readily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl, 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from trimethylsiloxy-terminated methylhydropolysiloxanes, trimethylsiloxy-terminated dimethylsiloxane/methylhydrosiloxane copolymers, and dimethylsiloxane/methylhydrosiloxane cyclic copolymers.

Compound (B) is in particular a diorganopolysiloxane containing at least two lower alkenyl groups (for example $C_2$-$C_4$ alkenyl groups); the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane/dimethylsiloxane copolymers, dimethylvinylsiloxy-terminated dimethylpolysiloxanes, dimethylvinylsiloxy-terminated dimethylsiloxane/methylphenylsiloxane copolymers, dimethylvinylsiloxy-terminated dimethylsiloxane/diphenylsiloxane/methylvinylsiloxane copolymers, trimethylsiloxy-terminated dimethylsiloxane/methylvinylsiloxane copolymers, trimethylsiloxy-terminated dimethylsiloxane/methylphenylsiloxane/methylvinylsiloxane copolymers, dimethylvinylsiloxy-terminated methyl(3,3,3-trifluoropropyl)polysiloxanes, and dimethylvinylsiloxy-terminated dimethylsiloxane/methyl(3,3,3-trifluoropropyl)siloxane copolymers.

In particular, the silicone elastomer may be obtained by reaction of dimethylvinylsiloxy-terminated dimethylpolysiloxane and of trimethylsiloxy-terminated methylhydropolysiloxane, in the presence of a platinum catalyst.

In particular, the sum of the number of ethylenic groups per molecule of compound (B) and of the number of hydrogen atoms bonded to silicon atoms per molecule of compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is notably chloroplatinic acid, chloroplatinic acid-olefin complexes, chloroplatinic acid-alkenylsiloxane complexes, chloroplatinic acid-diketone complexes, platinum black and platinum on a support.

Catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is preferably a non-emulsifying elastomer.

The term "non-emulsifying" defines silicone elastomers containing no hydrophilic chain, and in particular containing no polyoxyalkylene (notably polyoxyethylene or polyoxypropylene) units or polyglyceryl unit. Thus, according to a specific embodiment of the invention, the composition comprises a silicone elastomer that is free of polyoxyalkylene units and of polyglyceryl unit.

In particular, the silicone elastomer used in the present invention may be chosen from Dimethicone Crosspolymer (INCI name), Dimethicone/Vinyl Dimethicone Crosspolymer (INCI name), Dimethicone Crosspolymer-3 (INCI name).

Non-emulsifying elastomers are notably described in patents EP 242 219, EP 285 886 and EP 765 656.

The silicone elastomer is generally in a form conveyed in an oil (for example in the form of a gel), a paste or a powder.

In particular, the silicone elastomer particles may be conveyed in the form of a gel constituted of an organopolysiloxane elastomer included in at least one hydrocarbon-based oil and/or one silicone oil. In these gels, the organopolysiloxane particles are often non-spherical particles.

Preferably, the silicone elastomer is in the form of a gel in which said silicone elastomer is dispersed in a linear silicone oil (dimethicone) or cyclic silicone oil (e.g. decamethylcyclopentasiloxane), preferably in a linear silicone oil, or else in a volatile or nonvolatile, polar or nonpolar hydrocarbon-based oil.

According to a specific embodiment, use is made of a gel of silicone elastomer dispersed in a silicone oil chosen from a non-exhaustive list comprising decamethylcyclopentasiloxane (or cyclomethicone), polydimethylsiloxanes (PDMS or dimethicones), methyl trimethicone, phenyl methicone, phenyl dimethicone and phenyl trimethicone, preferably a linear silicone oil chosen from polydimethylsiloxanes (PDMS or dimethicones) with a viscosity ranging from 1 to 500 cSt at 25° C., optionally modified with optionally fluorinated aliphatic groups, or with functional groups such as hydroxyl, thiol and/or amine groups; and preferably unmodified.

According to another specific embodiment, use is made of a gel of silicone elastomer in a hydrocarbon-based oil, for example a volatile hydrocarbon-based oil, such as in particular isododecane, or non-volatile hydrocarbon-based oil such as for example mineral oils, such as squalane. Use may also be made of a gel of silicone elastomer in a polar non-volatile hydrocarbon-based oil, chosen in particular from esters, such as for example triethylhexanoin and vegetable oils.

As non-emulsifying elastomers, use may more particularly be made of those sold under the names KSG-6®, KSG-15®, KSG-16®, KSG-016F®, KSG-18®, KSG-41®, KSG-42®, KSG-43®, or KSG-44®, by the company Shin Etsu, DC9040®, DC9045®, DC9041 ®, Dow Corning EL-9240 Silicone Elastomer Blend, Dowsil™ EL-9241 DM Silicone Elastomer Blend, Dowsil™ EL-9140 DM Silicone Elastomer Blend by the company Dow Corning, SFE 839° by the company Momentive Performance Materials, and in particular the elastomer sold under the name KSG-43® by the company Shin Etsu.

The silicone elastomer particles may also be used in powder form; mention may in particular be made of the powders sold under the names Dow Corning 9505 Powder® and Dow Corning 9506 Powder® by the company Dow Corning, these powders having the INCI name: Dimethicone/Vinyl Dimethicone Crosspolymer.

The organopolysiloxane powder may also be coated with silsesquioxane resin, as described, for example, in patent U.S. Pat. No. 5,538,793. Such elastomer powders are sold under the names KSP-100®, KSP-101®, KSP-102®, KSP-103®, KSP-104®, KSP-105® by the company Shin-Etsu, and have the INCI name: Vinyl Dimethicone/Methicone Silsesquioxane Crosspolymer. As examples of organopolysiloxane powders coated with silsesquioxane resin that can be used according to the invention, mention may in particular be made of the reference KSP-100® from the company Shin-Etsu.

As silicone elastomer, mention may also be made of the compounds having the INCI name Dimethicone (and) Dimethicone/Vinyltrimethylsiloxysilicate Crosspolymer, such as that sold under the name Belsil REG 1102° by the company Wacker.

The elastomer may also be an emulsifying elastomer.

As emulsifying silicone elastomer, mention may be made of silicone polyether elastomers, polyglyceryl silicone elastomers, polyether dimethicone copolymers and mixtures thereof. The emulsifying silicone elastomers may include functional groups chosen from the group comprising polyglycerol, polyethylene glycol or polypropylene glycol. Mention may be made, for example, of Dimethicone (and) Dimethicone/PEG-10/15 Crosspolymer, sold under the name KSG-210®, and Dimethicone (and) Dimethicone/Polyglycerin-3 Crosspolymer, sold under the name KSG-710®, Squalane (and) Lauryl Dimethicone/Polyglycerin-3 Crosspolymer, sold under the name KSG-840®, mineral oil (and) Lauryl Dimethicone/Polyglycerin-3 Crosspolymer, sold under the name KSG-810°, triethylhexanoin (and) Lauryl Dimethicone/Polyglycerin-3 Crosspolymer, sold under the name KSG-830®, *Simmondsia Chinensis* (jojoba) oil (and) Lauryl Dimethicone/Polyglycerin-3 Crosspolymer, sold under the name X-22-6695B, by the company Shin Etsu.

Among the silicone elastomers, the compounds having the following INCI names will more particularly be considered Vinyl Dimethicone/Lauryl Dimethicone Crosspolymer, Dimethicone/PEG-10/15 Crosspolymer, Dimethicone/Polyglycerin-3 Crosspolymer, Dimethicone/Vinyl Dimethicone Crosspolymer, Dimethicone Crosspolymer, Dimethicone/Vinyltrimethylsiloxysilicate Crosspolymer, and their mixtures.

The following products will be more particularly considered:

- Triethylhexanoin (and) Vinyl Dimethicone/Lauryl Dimethicone Crosspolymer, such as for example KSG-43® from the company Shin Etsu;
- Dimethicone (and) Dimethicone/PEG-10/15 Crosspolymer, such as for example KSG-210® from the company Shin Etsu;
- Dimethicone (and) Dimethicone/Polyglycerin-3 Crosspolymer, such as for example KSG-710® from the company Shin Etsu;
- Dimethicone (and) Dimethicone/Vinyl Dimethicone Crosspolymer, such as for example KSG-16® from the company Shin Etsu;
- Dimethicone (and) Dimethicone Crosspolymer, such as for example Dowsil™ EL-9241 DM Silicone Elastomer Blend and Dowsil™ EL-9140 DM Silicone Elastomer Blend from the company Dow;
- Dimethicone (and) Dimethicone/Vinyltrimethylsiloxysilicate Crosspolymer, such as for example Belsil REG 1102® by the company Wacker.

Thus, as preferred silicone elastomer, mention may be made of Triethylhexanoin (and) Vinyl Dimethicone/Lauryl Dimethicone Crosspolymer (INCI name), Dimethicone (and) Dimethicone/PEG-10/15 Crosspolymer (INCI name), Dimethicone (and) Dimethicone/Polyglycerin-3 Crosspolymer (INCI name), Dimethicone (and) Dimethicone/Vinyl Dimethicone Crosspolymer (INCI name), Dimethicone (and) Dimethicone Crosspolymer (INCI name), Dimethicone Crosspolymer (INCI name) and Dimethicone (and) Dimethicone/Vinyltrimethylsiloxysilicate Crosspolymer (INCI name).

According to a preferred embodiment, the present invention relates to a composition, especially a cosmetic composition, in particular for making up and/or caring for keratin materials, comprising at least:

- one aqueous phase containing at least one non-particulate synthetic polymeric gelling agent;
- one oily phase containing at least:

(i) one silicone elastomer chosen from Vinyl Dimethicone/Lauryl Dimethicone Crosspolymer (INCI name), Dimethicone/PEG-10/15 Crosspolymer (INCI name), Dimethicone/Polyglycerin-3 Crosspolymer (INCI name), Dimethicone/Vinyl Dimethicone Crosspolymer (INCI name), Dimethicone Crosspolymer (INCI name) and Dimethicone/Vinyltrimethylsiloxysilicate Crosspolymer (INCI name);

(ii) one silicone resin; and (iii) one non-volatile silicone oil comprising at least one dimethicone group having a viscosity at 25° C. of greater than or equal to 9 centistokes (cSt) ($9\times10^{-6}$ $m^2/s$), measured according to the ASTM D-445 standard, and preferably one non-volatile phenyl silicone oil comprising at least one dimethicone group, optionally in mixture with a non-volatile ester oil.

Preferably, a composition according to the invention comprises, as silicone elastomer, Triethylhexanoin (and) Vinyl Dimethicone/Lauryl Dimethicone Crosspolymer (INCI name).

A composition according to the invention may comprise from 0.2% to 20% by weight, in particular from 0.3% to 18% by weight and preferably from 0.5% to 15% by weight of silicone elastomer(s), relative to the total weight of the composition.

Preferably, a composition according to the invention may comprise from 0.2% to 12% by weight, in particular from 0.3% to 11% by weight and preferably from 0.5% to 10% by weight of silicone elastomer(s), relative to the total weight of the composition.

It is understood that the contents of silicone elastomer(s) are given as a percentage of active material, or in other words as a percentage of solids.

Silicone Resin

As stated previously, the claimed compositions comprise at least one silicone resin, especially as detailed hereinbelow.

More generally, the term "resin" is intended to mean a compound of which the structure is three-dimensional. "Silicone resins" are also referred to as "siloxane resins". Thus, for the purposes of the present invention, a polydimethylsiloxane is not a silicone resin.

The nomenclature of silicone resins is known under the name "MDTQ", the resin being described as a function of the various siloxane monomer units that it comprises, each of the letters "MDTQ" characterizing a type of unit.

The letter "M" represents the Monofunctional unit of formula $R1R2R3SiO_{1/2}$, the silicon atom being bonded to only one oxygen atom in the polymer comprising this unit.

The letter "D" means a Difunctional unit $R1R2SiO_{2/2}$ in which the silicon atom is bonded to two oxygen atoms.

The letter "T" represents a Trifunctional unit of formula $R1SiO_{3/2}$.

Such resins are described, for example, in the *Encyclopedia of Polymer Science and Engineering*, vol. 15, John Wiley and Sons, New York, (1989), pp. 265-270, and U.S. Pat. Nos. 2,676,182, 3,627,851, 3,772,247, 5,248,739 or else U.S. Pat. Nos. 5,082,706, 5,319,040, 5,302,685 and 4,935,484.

In the units M, D and T defined previously, R, namely R1 and R2, represents a hydrocarbon-based radical (especially alkyl) containing from 1 to 10 carbon atoms, a phenyl group, a phenylalkyl group or else a hydroxyl group.

Finally, the letter "Q" means a tetrafunctional unit $SiO_{4/2}$ in which the silicon atom is bonded to four oxygen atoms, which are themselves bonded to the rest of the polymer.

Various silicone resins with different properties may be obtained from these different units, the properties of these polymers varying as a function of the type of monomers (or units), the nature and number of the radical R, the length of the polymer chain, the degree of branching and the size of the side chains.

As silicone resins that may be used in the compositions according to the invention, use may be made, for example, of silicone resins of MQ type, of T type or of MQT type.

MO Resins

As examples of silicone resins of MQ type, mention may be made of the alkylsiloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms or a hydroxyl group, preferably a methyl group.

As examples of solid silicone resins of MQ type of trimethylsiloxysilicate type, mention may be made of those sold under the reference SR1000® by the company Momentive Performance Materials, under the reference MQ 1600 by Dow Corning or under the reference TMS 803° by the company Wacker.

Mention may also be made, as silicone resins comprising MQ siloxysilicate units, of phenylalkylsiloxysilicate resins, such as phenylpropyldimethylsiloxysilicate, especially sold under the name Silshine 151° by the company General Electric. The preparation of such resins is described especially in patent U.S. Pat. No. 5,817,302.

T Resins

As examples of silicone resins of T type, mention may be made of the polysilsesquioxanes of formula $(RSiO_{3/2})_x$ (T units) in which x is greater than 100 and such that the group R is an alkyl group containing from 1 to 10 carbon atoms, it being possible for said polysilsesquioxanes to further comprise Si—OH end groups.

Preferably, use may be made of polymethylsilsesquioxane resins in which R represents a methyl group, for instance those sold:

- by the company Wacker under the reference Resin MK, such as Belsil PMS MK®: polymer comprising $CH_3SiO_{3/2}$ repeating units (T units), which may also comprise up to 1% by weight of $(CH_3)_2SiO_{2/2}$ units (D units) and having an average molecular weight of about 10 000 g/mol, or
- by the company Shin Etsu under the references KR-220L®, which are composed of T units of formula $CH_3SiO_{3/2}$ and contain Si—OH (silanol) end groups, under the reference KR-242A®, which comprise 98% of T units and 2% of dimethyl D units and contain Si—OH end groups, or else under the reference KR-251®, comprising 88% of T units and 12% of dimethyl D units and contain Si—OH end groups.

MQT Resins

Resins comprising MQT units that are especially known are those mentioned in document U.S. Pat. No. 5,110,890.

A preferred form of resins of MQT type are MQT-propyl (also known as MQTPr) resins. Such resins that can be used in the compositions according to the invention are especially those described and prepared in patent application WO 2005/075542.

The MQ-T-propyl resin preferably comprises the following units:

(i) $(R1_3SiO_{1/2})_a$;
(ii) $(R2_2SiO_{2/2})_b$;
(iii) $(R3SiO_{3/2})_c$; and
(iv) $(SiO_{4/2})_d$;

with:

- R1, R2 and R3 independently representing a hydrocarbon-based (especially alkyl) radical containing from 1 to 10 carbon atoms, a phenyl group, a phenylalkyl group or else a hydroxyl group and preferably an alkyl radical containing from 1 to 8 carbon atoms or a phenyl group,
- a being between 0.05 and 0.5,
- b being between zero and 0.3,
- c being greater than zero,
- d being between 0.05 and 0.6, $$-a+b+c+d=1, \text{ and } a, b, c \text{ and } d \text{ being mole fractions,}$$

on condition that more than 40 mol % of the groups R3 of the siloxane resin are propyl groups.

Preferably, the siloxane resin comprises the following units:

(i) $(R1_3SiO_{1/2})_a$;
(iii) $(R3SiO_{3/2})_c$; and
(iv) $(SiO_{4/2})_d$;

with:

- R1 and R3 independently representing an alkyl group containing from 1 to 8 carbon atoms, R1 preferably being a methyl group and R3 preferably being a propyl group,
- a being between 0.05 and 0.5, preferably between 0.15 and 0.4,
- c being greater than zero, preferably between 0.15 and 0.4,
- d being between 0.05 and 0.6, preferably between 0.2 and 0.6 or alternatively between 0.2 and 0.55, $$-a+b+c+d=1, \text{ and } a, b, c \text{ and } d \text{ being mole fractions,}$$

on condition that more than 40 mol % of the groups R3 of the siloxane resin are propyl groups.

The siloxane resins that can be used according to the invention may be obtained via a process comprising the reaction of:

A) an MQ resin comprising at least 80 mol % of units $(R1_3SiO_{1/2})_a$ and $(SiO_{4/2})_d$; with

- R1 representing an alkyl group containing from 1 to 8 carbon atoms, an aryl group, a carbinol group or an amino group,
- a and d being greater than zero,
- the ratio a/d being between 0.5 and 1.5;

and:

B) a T-propyl resin comprising at least 80 mol % of units $(R3SiO_{3/2})_c$; with

- R3 representing an alkyl group containing from 1 to 8 carbon atoms, an aryl group, a carbinol group or an amino group,
- c being greater than zero, on condition that at least 40 mol % of the groups R3 are propyl groups, wherein the weight ratio A/B is between 95:5 and 15:85 and preferably the weight ratio A/B is 30:70.

In particular, the weight ratio A/B is between 95:5 and 15:85. Preferably, the ratio A/B is less than or equal to 70:30. These preferred ratios have proven to allow comfortable deposits due to the absence of percolation of the rigid particles of MQ resin in the deposit. Thus, preferably, the silicone resin is chosen from the group comprising:

a) a resin of MQ type, chosen especially from (i) alkylsiloxysilicates, which may be trimethylsiloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkylsiloxysilicate resins, such as phenylpropyldimethylsiloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, it being possible for said polysilsesquioxanes to further comprise Si—OH end groups, and/or c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $(SiO_{4/2})_d$, with R1, R2 and R3 independently representing a hydrocarbon-based, especially alkyl, radical containing from 1 to 10 carbon atoms, a phenyl group, a phenylalkyl group or else a hydroxyl group and preferably an alkyl radical containing from 1 to 8 carbon atoms or a phenyl group, a being between 0.05 and 0.5, b being between zero and 0.3, c being greater than zero, d being between 0.05 and 0.6, $$-a+b+c+d=1, a, b, c \text{ and } d \text{ being mole fractions,}$$

on condition that more than 40 mol % of the groups R3 of the siloxane resin are propyl groups.

Thus, as silicone resins that are very particularly suitable for the invention, mention may in particular be made of silicone resins of MQ type, T type or MQT type, and more preferentially chosen from trimethylsiloxysilicate, polypropylsilsesquioxane, polymethylsilsesquioxane and their mixtures, preferably, trimethylsiloxysilicate, polypropylsilsesquioxane and their mixtures.

Preferably, a composition according to the invention may comprise, as silicone resin, at least one trimethylsiloxysilicate resin.

The silicone resin may be used in powder form, in a form dissolved in a solvent, usually chosen from apolar hydrocarbon-based oils or silicone oils, which are volatile or non-volatile, and preferably volatile.

Volatile hydrocarbon-based oils that may especially be mentioned include alkanes, preferably branched alkanes of 8 to 16 carbon atoms, especially such as $C_8$-$C_{16}$ isoalkanes (also known as isoparaffins), isododecane, isodecane and isohexadecane.

Volatile silicone oils that may be mentioned include linear or cyclic silicone oils, such as linear or cyclic polydimethylsiloxanes (PDMSs) containing from 3 to 7 silicon atoms. Examples of such oils that may be mentioned include decamethylcyclopentasiloxane, octamethylcyclotetrasiloxane, dodecamethylcyclohexasiloxane, decamethyltetrasiloxane, methyl trimethicone, polydimethylsiloxanes, such as those sold under the reference DC 200 by Dow Corning or else KF 96 A from Shin Etsu; alone or as mixtures.

In particular, said silicone resin(s) are present totally or partially, and preferably solely, in the oily phase.

Preferably, a composition according to the invention may comprise, as silicone resin, at least one resin chosen from the following compounds:

Polypropylsilsesquioxane (and) Isododecane, such as for example those sold under the reference Dowsil 680 ID Fluid® by the company Dow Corning, Isododecane (and) Trimethylsiloxysilicate, such as for example those sold under the references Silsoft 74, Silshine 151 by the company Momentive Performance Materials, and X-21-5595 and X-21-5616 by the company Shin Etsu, Dimethicone (and) Trimethylsiloxysilicate, such as for example those sold under the names KF-7312K, KF-7312L, X-21-5249L and X-21-5250L by the company Shin Etsu or Dow Corning 593 Fluid by the company Dow Corning, Trimethylsiloxysilicate (and) Polypropylsilsesquioxane, such as for example those sold under the name Dow Corning MQ-1640 Flake Resin by the company Dow Corning, Polymethylsilsesquioxane, Trimethylsiloxysilicate.

Thus, as silicone resins that are very particularly suitable for the invention, mention may in particular be made of silicone resins of MQ type, T type or MQT type, and more preferentially chosen from Polypropylsilsesquioxane (and) Isododecane, Dimethicone (and) Trimethylsiloxysilicate, Trimethylsiloxysilicate (and) Polypropylsilsesquioxane, Polymethylsilsesquioxane and Trimethylsiloxysilicate.

A composition according to the invention may comprise from 0.5% to 20% by weight, in particular from 0.6% to 18% by weight and preferably from 0.8% to 15% by weight of silicone resin(s), relative to the total weight of the composition.

It is understood that the contents of silicone resin(s) are given as a percentage of active material, or in other words as a percentage of solids.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) from 0.5% to 20% by weight of at least one silicone resin, relative to the total weight of the composition; and (iii) one non-volatile silicone oil comprising at least one dimethicone group having a viscosity at 25° C. of greater than or equal to 9 centistokes (cSt) ($9\times10^{-6}$ $m^2/s$), measured according to the ASTM D-445 standard.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) from 0.5% to 20% by weight of at least one silicone resin, relative to the total weight of the composition; and (iii) one non-volatile phenyl silicone oil comprising at least one dimethicone group.

Non-Volatile Silicone Oil Comprising at Least One Dimethicone Group and Non-Volatile Ester Oil A composition according to the invention comprises at least one non-volatile silicone oil comprising at least one dimethicone group, or a non-volatile ester oil, in particular chosen from triesters, or mixtures thereof.

The term "oil" means any fatty substance that is in liquid form at room temperature (25° C.) and atmospheric pressure (760 mmHg).

For the purposes of the present invention, the expression "non-volatile oil" is understood to mean an oil having a non-zero vapor pressure of less than 2.66 Pa, preferably less than 0.13 Pa, at room temperature (25° C.) and atmospheric pressure (760 mmHg). By way of example, the vapor pressure may be measured according to the static method or via the effusion method by isothermal thermogravimetry, depending on the vapor pressure (OCDE 104 standard).

In particular, a composition according to the invention comprises from 1% to 12% by weight, in particular from 1.5% to 10% by weight, and preferably from 2% to 8% by weight, of non-volatile silicone oil(s) comprising at least one dimethicone group, or of non-volatile ester oil(s), in particular chosen from triesters, or mixtures thereof, relative to the total weight of the composition.

It should be noted that if one of the ingredients of the composition is used in the presence of a non-volatile silicone oil or an ester oil mentioned above, such as for example the silicone elastomer and/or the silicone resin, then the content of these non-volatile oils takes into account the content(s) provided with said ingredient(s).

Preferably, a composition according to the invention comprises at least one non-volatile silicone oil comprising at least one dimethicone group, and more preferentially chosen from non-volatile phenyl silicone oils comprising at least one dimethicone group.

Non-Volatile Silicone Oil Comprising at Least One Dimethicone Group

The term "silicone oil" means an oil comprising at least one Si atom.

The non-volatile silicone oil according to the invention have a viscosity at 25° C. of greater than or equal to 9 centistokes (cSt) ($9\times10^{-6}$ $m^2/s$), measured according to the ASTM D-445 standard.

The non-volatile silicone oil that can be used in the invention may especially be chosen from silicone oils especially with a viscosity at 25° C. of greater than or equal to 9 centistokes (cSt) ($9\times10^{-6}$ $m^2/s$) and less than 800 000 cSt, preferably between 50 and 600 000 cSt and preferably between 100 and 500 000 cSt. The viscosity of this silicone may be measured according to the ASTM D-445 standard.

For the purposes of the present invention, the expression "non-volatile silicone oil" is understood to mean a silicone oil having a non-zero vapor pressure of less than 2.66 Pa, preferably less than 0.13 Pa, at room temperature (25° C.) and atmospheric pressure (760 mmHg). By way of example, the vapor pressure may be measured according to the static method or via the effusion method by isothermal thermogravimetry, depending on the vapor pressure (OCDE 104 standard). According to a first embodiment, the non-volatile silicone oil is a non-phenyl silicone oil comprising at least one dimethicone group.

The term "dimethicone group" denotes a divalent siloxane group in which the silicon atom bears two methyl radicals, this group not being located at the ends of the molecule. It may be represented by the following formula: $—(Si(CH_3)_2—O)—$.

The expression "non-phenyl silicone oil" denotes a silicone oil comprising no phenyl substituents.

The non-volatile non-phenyl silicone oil comprising at least one dimethicone group may be chosen from:

non-volatile polydimethylsiloxanes (PDMSs),

PDMSs including alkyl or alkoxy groups, which are on the side and/or at the ends of the silicone chain, these groups each containing from 2 to 24 carbon atoms, and PDMSs including aliphatic and/or aromatic groups, or functional groups such as hydroxyl, thiol and/or amine groups.

According to one embodiment, a composition according to the invention contains at least one non-phenyl silicone oil comprising at least one dimethicone group, in particular such as a linear (i.e. noncyclic) oil.

Representative examples of these non-volatile and non-phenyl linear silicone oils that may be mentioned include polydimethylsiloxanes and alkyldimethicones.

The non-phenyl silicone oil comprising at least one dimethicone group may notably be chosen from the silicones of formula:

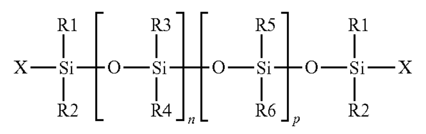

wherein:

the substituents R1 to R6 and X represent a methyl group, and p and n are integers such that the viscosity is 500 000 cSt, such as the product sold under the name SE30® by the company M, the product sold under the name AK 500000® by the company Wacker, the product sold under the name Mirasil® DM 500000 by the company Bluestar, and the product sold under the name Dow Corning 200 Fluid® 500000 cSt by the company Dow Corning; or the substituents R1 to R6 and X represent a methyl group, and p and n are integers such that the viscosity is 60 000 cSt, such as the product sold under the name Dow Corning 200 Fluid® 60000 CS by the company Dow Corning, and the product sold under the name Wacker Belsil® DM 60000 by the company Wacker; or the substituents R1 to R6 and X represent a methyl group, and p and n are integers such that the viscosity is 350 cSt, such as the product sold under the name Dow Corning 200 Fluid® 350 CS by the company Dow Corning; or the substituents R1 to R6 represent a methyl group, the group X represents a hydroxyl group, and n and p are integers such that the viscosity is 700 cSt, such as the product sold under the name Baysilone Fluid T0.7® by the company Momentive.

As another non-volatile non-phenyl silicone oil that can be used within the context of the invention, mention may also be made of the product sold under the name Belsil® DM100 by the company Wacker.

According to another embodiment, a composition according to the invention preferably contains at least one non-volatile phenyl silicone oil comprising at least one dimethicone group.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) one silicone resin; and (iii) one non-volatile phenyl silicone oil comprising at least one dimethicone group.

The expression "phenyl silicone oil" denotes a silicone oil bearing at least one phenyl substituent.

As representative examples of these non-volatile phenyl silicone oils comprising a dimethicone group, mention may more particularly be made of phenyl dimethicones, diphenyl dimethicones, and mixtures thereof.

As phenyl silicone oil comprising a dimethicone group, use may in particular be made of diphenyl dimethicones such as the Belsil® oils, in particular Belsil PDM 1000® (1000 cSt), Belsil PDM 200® (200 cSt) and Belsil PDM 20® (20 cSt) from Wacker. The values in parentheses represent the viscosities at 25° C.

Use may preferably be made of Trimethyl Siloxyphenyl Dimethicone, sold notably under the reference Belsil PDM 1000® by the company Wacker.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) one silicone resin; and (iii) one non-volatile silicone oil comprising at least one dimethicone group having a viscosity at 25° C. of greater than or equal to 9 centistokes (cSt) ($9\times10^{-6}$ $m^2/s$), measured according to the ASTM D-445 standard.

Non-Volatile Ester Oil

The non-volatile ester oils have in particular between 18 and 70 carbon atoms.

The ester oils may be hydroxylated.

The non-volatile ester oil may in particular be chosen from:

- monoesters comprising between 18 and 40 carbon atoms in total, in particular the monoesters of formula $R_1COOR_2$ in which $R_1$ represents a linear or branched fatty acid residue including from 4 to 40 carbon atoms and $R_2$ represents a hydrocarbon-based chain, which is notably branched, containing from 4 to 40 carbon atoms, on condition that $R_1+R_2$ is greater than or equal to 18, for instance Purcellin oil (cetostearyl octanoate), isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate. Preferably, they are esters of formula $R_1COOR_2$ in which $R_1$ represents a linear or branched fatty acid residue including from 4 to 40 carbon atoms and $R_2$ represents a hydrocarbon-based chain that is notably branched, containing from 4 to 40 carbon atoms, $R_1$ and $R_2$ being such that $R_1+R_2$ is greater than or equal to 18. Preferably, the ester comprises between 18 and 40 carbon atoms in total. Preferred monoesters that may be mentioned include isononyl isononanoate, oleyl erucate and/or 2-octyldodecyl neopentanoate;
- diesters, such as those comprising between 18 and 60 carbon atoms in total and in particular between 18 and 50 carbon atoms in total. It is notably possible to use diesters of a dicarboxylic acid and of monoalcohols, such as diisostearyl malate, or glycol diesters of monocarboxylic acids, such as neopentyl glycol diheptanoate or polyglyceryl-2 diisostearate, such as the compound sold under the trade reference Dermol DGDIS® by the company Alzo;
- triesters, in particular comprising between 35 and 70 carbon atoms in total, in particular such as triesters of a tricarboxylic acid, such as triisostearyl citrate, or tridecyl trimellitate, or glycol triesters of monocarboxylic acids, such as polyglyceryl-2 triisostearate;
- tetraesters, notably with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, polyglyceryl-2 tetraisostearate or else pentaerythrityl tetrakis(2-decyl)tetradecanoate;
- polyesters obtained by condensation of unsaturated fatty acid dimer and/or trimer and of diol, such as those described in patent application FR 0 853 634, in particular such as of dilinoleic acid and of 1,4-butanediol. Mention may especially be made in this respect of the polymer sold by Biosynthis under the name Viscoplast 14436H® (INCI name: dilinoleic acid/butanediol copolymer), or else copolymers of polyols and of diacid dimers, and esters thereof, such as Hailuscent ISDA®;
- esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid notably of $C_8$ to $C_{34}$, notably of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;
- polyol esters and pentaerythritol esters, such as dipentaerythrityl tetrahydroxystearate/tetraisostearate,
- and mixtures thereof.

Preferably, a composition according to the invention comprises at least one non-volatile ester oil, preferentially chosen from triesters.

In particular, the non-volatile ester oil is chosen from triesters of a tricarboxylic acid, more particularly triisostearyl citrate and tridecyl trimellitate, and glycol triesters of monocarboxylic acids, more particularly polyglycerol-2 triisostearate.

Preferably, the non-volatile ester oil is tridecyl trimellitate.

Aqueous Phase

The aqueous phase of a composition according to the invention comprises water and optionally a water-soluble solvent.

The aqueous phase of a composition according to the invention comprises in particular water at a content of between 40% and 80% by weight, in particular between 45% and 78% by weight, and preferably between 50% and 75% by weight, relative to the total weight of the composition.

According to a preferred embodiment, the present invention relates to a composition, especially a cosmetic composition, in particular for making up and/or caring for keratin materials, comprising at least:

one aqueous phase comprising water at a content of between 40% and 80% by weight, relative to the total weight of the composition, and containing at least one non-particulate synthetic polymeric gelling agent;

one oily phase containing at least:

(i) one silicone elastomer;

(ii) one silicone resin; and (iii) one non-volatile silicone oil comprising at least one dimethicone group having a viscosity at 25° C. of greater than or equal to 9 centistokes (cSt) ($9\times10^{-6}$ $m^2/s$), measured according to the ASTM D-445 standard.

According to a preferred embodiment, the present invention relates to a composition, especially a cosmetic composition, in particular for making up and/or caring for keratin materials, comprising at least:

one aqueous phase comprising water at a content of between 40% and 80% by weight, relative to the total weight of the composition, and containing at least one non-particulate synthetic polymeric gelling agent;

one oily phase containing at least:

(i) one silicone elastomer;

(ii) one silicone resin; and (iii) one non-volatile phenyl silicone oil comprising at least one dimethicone group.

In the present invention, the term "water-soluble solvent" denotes a compound that is liquid at room temperature (25° C.) and water-miscible (miscibility with water of greater than 50% by weight at 25° C. and atmospheric pressure (760 mmHg)).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms such as ethanol and isopropanol, glycols containing from 2 to 8 carbon atoms such as ethylene glycol, propylene glycol, 1,3-butylene glycol and dipropylene glycol, $C_3$ and $C_4$ ketones and $C_2$-$C_4$ aldehydes.

According to another embodiment variant, the aqueous phase of a composition according to the invention may comprise at least one $C_2$-$C_{32}$ polyol.

For the purposes of the present invention, the term "polyol" should be understood as meaning any organic molecule including at least two free hydroxyl groups.

Preferably, a polyol in accordance with the present invention is present in liquid form at room temperature (25° C.).

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols that are suitable for formulating a composition according to the present invention are those in particular containing from 2 to 32 carbon atoms and preferably 3 to 16 carbon atoms.

In particular, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerin, polyglycerols, such as glycerol oligomers, for instance diglycerol, polyethylene glycols, and mixtures thereof.

According to one preferred embodiment of the invention, said polyol is chosen from ethylene glycol, pentaerythritol, trimethylolpropane, propylene glycol, dipropylene glycol, glycerin, polyglycerols, polyethylene glycols, and mixtures thereof.

In particular, a composition according to the invention comprises from 1% to 22% by weight, in particular from 5% to 20% by weight and preferably from 10% to 18% by weight of polyol(s) relative to the total weight of the composition.

Thus, according to one of its aspects, the present invention relates to a composition, especially a cosmetic composition, in particular for making up and/or caring for keratin materials, comprising at least:

one aqueous phase containing at least one non-particulate synthetic polymeric gelling agent;

one oily phase containing at least:

(i) one silicone elastomer;

(ii) one silicone resin;

(iii) one non-volatile silicone oil comprising at least one dimethicone group, or one non-volatile ester oil, or mixtures thereof; and from 10% to 18% by weight of polyol(s) relative to the total weight of the composition.

Preferably, a composition according to the invention further comprises at least one polyol, preferably at least one $C_2$-$C_8$ liquid polyol.

More preferentially, the composition of the invention comprises at least glycerin.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

glycerin;

one oily phase containing at least:

(i) one silicone elastomer;

(ii) one silicone resin; and (iii) one non-volatile silicone oil comprising at least one dimethicone group having a viscosity at 25° C. of greater than or equal to 9 centistokes (cSt) ($9\times10^{-6}$ $m^2/s$), measured according to the ASTM D-445 standard.

According to a preferred embodiment, the present invention relates to a composition, especially a cosmetic composition, in particular for making up and/or caring for keratin materials, comprising at least:

one aqueous phase containing at least one non-particulate synthetic polymeric gelling agent;

glycerin;

one oily phase containing at least:

(i) one silicone elastomer;

(ii) one silicone resin; and (iii) one non-volatile phenyl silicone oil comprising at least one dimethicone group.

Colorant

A composition in accordance with the present invention may comprise at least one colorant, which may be chosen from particulate or non-particulate, water-soluble or water-insoluble, liposoluble or non-liposoluble, organic or inorganic colorants, materials with an optical effect, and mixtures thereof.

A composition according to the invention may comprise from 0.1% to 10% by weight, in particular from 0.5% to 8% by weight and preferably from 1% to 6% by weight of colorant(s), relative to the total weight of the composition.

For the purposes of the present invention, the term "colorant" means a compound that is capable of producing a colored optical effect when it is formulated in sufficient amount in a suitable cosmetic medium.

The colorants that are suitable for use in the invention may be water-soluble, but may also be liposoluble.

For the purposes of the invention, the term "water-soluble colorant" means any natural or synthetic, generally organic compound, which is soluble in an aqueous phase or water-miscible solvents and which is capable of imparting color. In particular, the term "water-soluble" is intended to characterize the capacity of a compound to be dissolved in water, measured at 25° C., to a concentration at least equal to 0.1 g/l (production of a macroscopically isotropic, transparent, colored or colorless solution). This solubility is in particular greater than or equal to 1 g/l.

As water-soluble dyes that are suitable for use in the invention, mention may be made in particular of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As nonlimiting illustrations of sources of water-soluble colorant(s) capable of being used in the context of the present invention, mention may notably be made of those of natural origin, such as extracts of cochineal carmine, of beetroot, of grape, of carrot, of tomato, of annatto, of paprika, of henna, of caramel and of curcumin.

Thus, the water-soluble colorants that are suitable for use in the invention are notably carminic acid, betanin, anthocyanins, enocyanins, lycopene, beta-carotene, bixin, norbixin, capsanthin, capsorubin, flavoxanthin, lutein, cryptoxanthin, rubixanthin, violaxanthin, riboflavin, rhodoxanthin, canthaxanthin, chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble colorants are notably permitted for food use. Representatives of these dyes that may be mentioned more particularly include dyes of the carotenoid family, referenced under the food codes E120, E162, E163, E160a-g, E150a, E101, E100, E140 and E141.

According to a particular variant, the water-soluble colorant(s) that are to be transferred onto the skin and/or the lips intended to be made up are formulated in a physiologically acceptable medium so as to be compatible with impregnation into the substrate.

For the purposes of the invention, the term "liposoluble colorant" is intended to mean any natural or synthetic, generally organic compound, which is soluble in an oily phase or in solvents that are miscible with a fatty substance, and which is capable of imparting color.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes ((3-carotene, lycopene), xanthophylls (capsanthin, capsorubin, lutein), palm oil, Sudan brown, quinoline yellow, annatto and curcumin.

Among the colorants, mention may also be made of pigments, nacres and/or particles with a metallic glint. Preferably, a composition according to the invention comprises at least pigments.

The term "pigments" should be understood as meaning white or colored, inorganic (mineral) or organic particles, which are insoluble in an aqueous solution, and which are intended to color and/or opacify the composition containing them and/or the deposit produced with the composition.

The pigments may be white or colored. They may be chosen from mineral pigments, organic pigments and composite pigments (i.e. pigments based on mineral and/or organic materials).

The pigments may be chosen from monochromic pigments, lakes, nacres, and pigments with an optical effect, for instance reflective pigments and goniochromatic pigments.

The pigments may for example be in pigment powder or paste form. They may be coated or uncoated.

The mineral pigments may be chosen from metal oxide pigments, chromium oxides, iron oxides, titanium dioxide, zinc oxides, cerium oxides, zirconium oxides, manganese violet, Prussian blue, ultramarine blue, ferric blue, and mixtures thereof.

They may also be pigments having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is that sold by the company Miyoshi under the reference PC Ball PC-LL-100 P, this pigment being constituted of silica microspheres containing yellow iron oxide.

Preferably, the composition according to the invention may comprise pigments chosen from iron oxides and/or titanium dioxides.

The organic pigments may for example be cochineal carmine; organic pigments of azo, anthraquinone, indigoid, xanthene, pyrene, quinoline, triphenylmethane or fluoran dyes; organic lakes or insoluble sodium, potassium, calcium, barium, aluminum, zirconium, strontium or titanium salts of acidic dyes such as azo, anthraquinone, indigoid, xanthene, pyrene, quinoline, triphenylmethane or fluoran dyes. These dyes generally include at least one carboxylic or sulfonic acid group; and melanin-based pigments.

Among the organic pigments, mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 and FD&C Yellow No. 6.

For the purposes of the present patent application, the term "nacre" means colored particles of any form, which may or may not be iridescent, notably produced by certain molluscs in their shell, or alternatively synthesized, and which exhibit a color effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye notably of the abovementioned type, and also nacreous pigments based on bismuth oxychloride. They may also be mica particles, at the surface of which are superposed at least two successive layers of metal oxides and/or of organic colorants.

The nacres may more particularly have a yellow, pink, red, bronze, orange, brown, gold and/or coppery color or glint.

As illustrations of nacres that may be introduced as interference pigments into the first composition, mention may be made of the gold-colored nacres notably sold by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres notably sold by the company Merck under the name Bronze fine (17384) (Colorona) and Bronze (17353) (Colorona) and by the company Engelhard under the name Super bronze (Cloisonne); the orange nacres notably sold by the company Engelhard under the name Orange 363C (Cloisonne) and Orange MCR 101 (Cosmica) and by the company Merck under the name Passion orange (Colorona) and Matte orange (17449) (Microna); the brown nacres notably sold by the company Engelhard under the name Nu-antique copper 340XB (Cloisonne) and Brown CL4509 (Chromalite); the nacres with a coppery glint notably sold by the company Engelhard under the name Copper 340A (Timica); the nacres with a red glint notably sold by the company Merck under the name Sienna fine (17386) (Colorona); the nacres with a yellow glint notably sold by the company Engelhard under the name Yellow (4502) (Chromalite); the red nacres with a gold glint notably sold by the company Engelhard under the name Sunstone G012 (Gemtone); the pink nacres notably sold by the company Engelhard under the name Tan opale G005 (Gemtone); the black nacres with a gold glint notably sold by the company Engelhard under the name Nu antique bronze 240 AB (Timica), the blue nacres notably sold by the company Merck under the name Matte blue (17433) (Microna), the white nacres with a silvery glint notably sold by the company Merck under the name Xirona Silver, and the golden-green pink-orange nacres notably sold by the company Merck under the name Indian summer (Xirona), and mixtures thereof.

For the purposes of the present invention, the term "particles with a metallic glint" means any compound whose nature, size, structure and surface finish allow it to reflect incident light, in particular in a non-iridescent manner.

The particles with a metallic glint that may be used in the invention are in particular chosen from:

- particles of at least one metal and/or of at least one metal derivative;
- particles comprising a monomaterial or multimaterial organic or mineral substrate, at least partially coated with at least one layer with a metallic glint comprising at least one metal and/or at least one metal derivative; and
- mixtures of said particles.

Among the metals that may be present in said particles, mention may for example be made of Ag, Au, Cu, Al, Ni, Sn, Mg, Cr, Mo, Ti, Zr, Pt, Va, Rb, W, Zn, Ge, Te, Se, and mixtures or alloys thereof. Ag, Au, Cu, Al, Zn, Ni, Mo, Cr, and mixtures or alloys thereof (for example bronzes and brasses) are preferred metals.

The term "metal derivatives" denotes compounds derived from metals, in particular oxides, fluorides, chlorides and sulfides.

Illustrations of these particles that may be mentioned include aluminum particles, such as those sold under the names Starbrite 1200 EAC® by the company Siberline and Metalure® by the company Eckart and glass particles coated with a metallic layer, especially those described in documents JPH09188830, JPH10158450, JPH10158541 and JPH07258460.

Hydrophobic Treatment of the Colorants

The pulverulent colorants as described above can be surface-treated, totally or partially, with a hydrophobic agent.

Hydrophobic-treated pigments are notably described in document EP 1 086 683. The hydrophobic-treatment agent may be chosen from silicones such as for example methicones and dimethicones, perfluoroalkylsilanes, silanes, fatty acids such as stearic acid, metal soaps such as aluminum dimyristate and the aluminum salt of hydrogenated tallow glutamate, perfluoroalkyl phosphates, polyhexafluoropropylene oxides, perfluoropolyethers, amino acids, N-acyl amino acids or salts thereof, lecithin, isopropyl triisostearyl titanate, isostearyl sebacate, and mixtures thereof.

The term "alkyl" mentioned in the compounds cited above especially denotes an alkyl group containing from 1 to 30 carbon atoms, preferably containing from 5 to 16 carbon atoms. Preferably, a composition according to the invention comprises at least one, preferably pulverulent, colorant, in particular chosen from pigments, and preferably from untreated mineral pigments, hydrophobic-treated mineral or organic pigments, and mixtures thereof.

Additional Compounds

Oils

A composition according to the invention may comprise at least one other oil different from the oils described above.

Thus, a composition according to the invention may comprise hydrocarbon-based oils, silicone oils, fluorinated or nonfluorinated oils, or mixtures thereof.

The oils may be volatile or nonvolatile.

They may be of animal, plant, mineral or synthetic origin.

The term "fluorinated oil" is intended to mean an oil comprising at least one fluorine atom.

The term "hydrocarbon-based oil" is intended to mean an oil mainly containing hydrogen and carbon atoms. The oils may optionally comprise oxygen, nitrogen, sulfur and/or phosphorus atoms, for example in the form of hydroxyl or acid radicals.

The term "apolar hydrocarbon-based oil" or "hydrocarbon oil" means an oil containing only hydrogen and carbon atoms.

For the purposes of the invention, the term "volatile oil" is intended to mean any oil that is capable of evaporating on contact with the skin in less than one hour, at room temperature (25° C.) and atmospheric pressure (760 mmHg). The volatile compound is a volatile cosmetic compound that is liquid at room temperature, especially having a non-zero vapor pressure, at room temperature (25° C.) and atmospheric pressure (760 mmHg), especially having a vapor pressure ranging from 2.66 Pa to 40 000 Pa (0.02 to 300 mmHg), in particular ranging from 2.66 Pa to 13 000 Pa (0.02 to 100 mmHg) and more particularly ranging from 2.66 Pa to 1300 Pa (0.02 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof. Preferably, the volatile hydrocarbon-based oil is chosen from volatile hydrocarbon-based oils containing from 8 to 16 carbon atoms and mixtures thereof, in particular from isododecane, isodecane and isohexadecane, and is especially isododecane.

Mention may also be made of volatile linear alkanes comprising from 8 to 16 carbon atoms, in particular from 10 to 15 carbon atoms and more particularly from 11 to 13 carbon atoms, for example n-dodecane ($C_{12}$) and n-tetradecane ($C_{14}$) sold by Sasol under the respective references Parafol® 12-97 and Parafol® 14-97, and also mixtures thereof, the undecane-tridecane mixture, mixtures of n-undecane ($C_{11}$) and of n-tridecane ($C_{13}$) obtained in examples 1 and 2 of application WO 2008/155059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane, cyclohexasiloxane and dodecamethylcyclohexasiloxane, and in particular cyclohexasiloxane.

According to one embodiment, a composition according to the invention comprises at least one volatile silicone oil.

In particular, a composition according to the invention may comprise from 0.1% to 8% by weight, preferably from 0.2% to 6% by weight and more preferentially from 0.5% to 5% by weight of volatile silicone oil(s), relative to the total weight of the composition.

According to another embodiment variant, a composition according to the invention comprises no volatile silicone oil(s).

According to a preferred embodiment variant, a composition according to the invention may comprise at least one volatile oil, preferably at least one volatile hydrocarbon-based oil, and more preferentially at least one volatile hydrocarbon-based oil having from 8 to 16 carbon atoms.

In particular, a composition according to the invention may comprise from 0.1% to 5% by weight, preferably from 0.2% to 4.5% by weight, and more preferentially from 0.5% to 4% by weight of volatile hydrocarbon-based oil(s) having from 8 to 16 carbon atoms, preferably isododecane, relative to the total weight of the composition.

In the case where one of the ingredients of the composition is used in the presence of one or more volatile oils, such as for example the silicone elastomer and/or the silicone resin, then the content of volatile oil(s) is evaluated on all of these oils present.

Non-Volatile Oils

The non-volatile oils may in particular be chosen from hydrocarbon-based oils and/or fluorinated oils and/or silicone oils.

Non-volatile hydrocarbon-based oils that may especially be mentioned include:

- hydrocarbon-based oils of animal origin,
- hydrocarbon-based oils of plant origin, synthetic ethers containing from 10 to 40 carbon atoms, such as dicaprylyl ether,
- apolar hydrocarbon-based oils of mineral or synthetic origin, in particular liquid paraffin or derivatives thereof, liquid petroleum jelly, polybutylenes, hydrogenated polyisobutylenes, decene/butene copolymers, polybutene/polyisobutene copolymers, polydecenes and hydrogenated polydecenes, and mixtures thereof, and preferably hydrogenated polyisobutene,
- fatty alcohols that are liquid at room temperature (25° C.) with a branched and/or unsaturated carbon-based chain containing from 12 to 26 carbon atoms, for instance 2-octyldodecanol, isostearyl alcohol and oleyl alcohol,
- $C_{12}$-$C_{22}$ higher fatty acids such as oleic acid, linoleic acid, linolenic acid, and mixtures thereof, and
- phenyl silicone oils, such as for example phenyl trimethicones, diphenylsiloxy phenyl trimethicones, trimethyl pentaphenyl trisiloxane, and mixtures thereof, and also mixtures of these various oils.

Surfactant

According to a preferred embodiment, the composition according to the invention may also comprise at least one surfactant.

The surfactants may be chosen from nonionic, anionic, cationic and amphoteric surfactants, and mixtures thereof. Reference may be made to Kirk-Othmer's *Encyclopedia of Chemical Technology*, Volume 22, pages 333-432, 3rd Edition, 1979, Wiley, for the definition of the emulsifying properties and functions of surfactants, in particular pages 347-377 of this reference, for the anionic, amphoteric and nonionic surfactants.

Nonionic Surfactant

Preferably, the composition according to the invention comprises at least one nonionic surfactant.

The nonionic surfactants may notably be chosen from alkyl and polyalkyl esters of poly(ethylene oxide), oxyalkylenated alcohols, alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, optionally polyoxyethylenated alkyl and polyalkyl ethers of glycerol, gemini surfactants, cetyl alcohol, stearyl alcohol, and mixtures thereof.

Oxyalkylenated, in particular oxyethylenated and/or oxypropylenated, alcohols that are preferably used are those that may include from 1 to 150 oxyethylene and/or oxypropylene units, in particular containing from 20 to 100 oxyethylene units, in particular notably $C_8$-$C_{24}$ and preferably $C_{12}$-$C_{18}$ fatty alcohols; it being possible for these to optionally be ethoxylated, for instance stearyl alcohol ethoxylated with 20 oxyethylene units (CTFA name Steareth-20), for instance Brij® 78 sold by the company Uniqema, cetearyl alcohol ethoxylated with 30 oxyethylene units (CTFA name Ceteareth-30), and the mixture of $C_{12}$-$C_{15}$ fatty alcohols including 7 oxyethylene units (CTFA name $C_{12-15}$ Pareth-7), for instance the product sold under the name Neodol 25-7® by Shell Chemicals; or in particular oxyalkylenated (oxyethylenated and/or oxypropylenated) alcohols containing from 1 to 15 oxyethylene and/or oxypropylene units, in particular ethoxylated $C_8$-$C_{24}$ and preferably $C_{12}$-$C_{18}$ fatty alcohols, such as stearyl alcohol ethoxylated with 2 oxyethylene units (CTFA name Steareth-2), for instance Brij® 72 sold by the company Uniqema.

Optionally polyoxyethylenated alkyl and polyalkyl esters of sorbitan that are preferably used include those with a number of ethylene oxide (EO) units ranging from 0 to 100. Examples that may be mentioned include sorbitan laurate 4 or 20 EO, in particular polysorbate 20 (or polyoxyethylene (20) sorbitan monolaurate) such as the product Tween® 20 sold by the company Uniqema, or else polysorbate 60, sorbitan palmitate 20 EO, sorbitan isostearate, sorbitan stearate 20 EO, sorbitan oleate 20 EO, or else the Cremophor® products (RH 40, RH 60, etc.) from BASF. The mixture of sorbitan stearate and of sucrose cocoate, sold under the name Arlacel® 2121U-FL from Croda, may also be mentioned.

Alkyl and polyalkyl glucosides or polyglucosides that are preferably used include those containing an alkyl group including from 6 to 30 carbon atoms and preferably from 6 to 18 or even from 8 to 16 carbon atoms, and containing a glucoside group preferably comprising from 1 to 5 and notably 1, 2 or 3 glucoside units. The alkyl polyglucosides may be chosen, for example, from decyl glucoside (alkyl-$C_9/C_{11}$-polyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, for instance the product sold under the name Plantacare KE 3711® by the company Cognis or Oramix CG 110® by the company SEPPIC; lauryl glucoside, for instance the product sold under the name Plantacare 1200 UP® by the company Henkel or Plantaren 1200 N® by the company Henkel; cocoyl glucoside, for instance the product sold under the name Plantacare 818 UP® by the company Henkel; caprylyl glucoside, for instance the product sold under the name Plantacare 810 UP® by the company Cognis; the mixture of arachidyl glucoside and behenyl alcohol and arachidyl alcohol, the INCI name of which is Arachidyl Alcohol (and) Behenyl Alcohol (and) Arachidyl Glucoside, sold under the name Montanov® 202 by the company SEPPIC; and mixtures thereof.

Anionic Surfactant

The anionic surfactants may be chosen from alkyl ether sulfates, carboxylates, amino acid derivatives, sulfonates, isethionates, taurates, sulfosuccinates, alkylsulfoacetates, phosphates and alkyl phosphates, polypeptides, metal salts of $C_{10}$-$C_{30}$ and especially $C_{16}$-$C_{25}$ fatty acids, in particular metal stearates and behenates, and mixtures thereof.

Cationic Surfactant

The cationic surfactants may be chosen from alkylimidazolidiniums, such as isostearyl ethylimidonium ethosulfate, ammonium salts such as ($C_{12-30}$-alkyl)-tri($C_{1-4}$-alkyl)ammonium halides such as N,N,N-trimethyl-1-docosanaminium chloride (or behentrimonium chloride).

Amphoteric Surfactant

The compositions according to the invention may also contain one or more amphoteric surfactants, for instance N-acyl amino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

Silicone Surfactant

The composition may also comprise at least one silicone surfactant. By way of example, as nonionic surfactants with an HLB of greater than or equal to 8 at 25° C., used alone or as a mixture, mention may be made of dimethicone copolyol or dimethicone copolyol benzoate, and as nonionic surfactants with an HLB of less than 8 at 25° C., used alone or as a mixture, mention may be made of a cyclomethicone/dimethicone copolyol mixture.

As silicone surfactant, mention may be made of PEG-10 Dimethicone sold under the name KF-6017® by Shin Etsu, Dimethicone (and) PEG/PPG-18/18 Dimethicone sold under the name ES-5226 DM® by the company Dow Corning Corporation, PEG-9 Polydimethylsiloxyethyl Dimethicone (and) PEG-9 sold under the name KF-6028®, and Lauryl PEG-9 Polydimethylsiloxyethyl Dimethicone sold under the name KF-6038®, by the company Shin Etsu.

Preferably, the composition according to the invention comprises at least one nonionic surfactant.

Preferably, the composition according to the invention comprises at least one surfactant chosen from optionally polyoxyethylenated alkyl and polyalkyl esters of sorbitan, alkyl and polyalkyl glucosides or polyglucosides, stearyl alcohol, and mixtures thereof.

Preserving Agent

According to one embodiment, the composition according to the invention may also comprise at least one preserving agent.

The preserving agent is a preserving agent usually used in cosmetics. It may be chosen from the positive list contained in Annex V of Regulation (EC) No 1223/2009, which specifies the list of preserving agents permitted in cosmetics. The role of these ingredients is to stabilize the formula from a bacteriological point of view.

Thus, as preserving agents, use may be made of any preserving agent usually used in the field under consideration, such as for example para-hydroxybenzoic acid esters, also referred to as Parabens®, for example propylparaben, methylparaben, butylparaben, ethylparaben or isobutylparaben, phenoxyethanol, formaldehyde generators, for instance imidazolidinylurea or diazolidinylurea, disodium EDTA, tetrasodium EDTA, sodium benzoate, sodium dehydroacetate, potassium sorbate, benzoic acid, benzyl alcohol, chlorophenesin, chlorhexidine digluconate, alkyltrimethylammonium bromide such as myristyltrimethylammonium bromide (CTFA name: Myrtrimonium bromide), dodecyltrimethylammonium bromide, hexadecyltrimethylammonium bromide and mixtures thereof, such as the mixture sold under the name Cetrimide® by the company FEF CHEMICALS, or else polymer quaternary ammonium salts, such as polyquatemium-10, and in particular phenoxyethanol and/or sodium dehydroacetate.

A composition according to the invention may comprise from 0.001% to 5% by weight, preferably from 0.1% to 1.5% by weight of preserving agent(s), in particular of phenoxyethanol, relative to the total weight of the composition.

Usual Additional Cosmetic Ingredient

A composition used according to the invention may also comprise any usual cosmetic ingredient, which may be notably chosen from fillers, cosmetic active agents, antioxidants, additional lipophilic or hydrophilic film-forming polymers, solid fatty substances, such as paste fatty substances and waxes, fragrances, neutralizers, sunscreens, sweeteners, vitamins, free-radical scavengers, sequestrants, and mixtures thereof.

The composition may thus comprise at least one active agent chosen from moisturizers, cicatrizing agents and/or antiaging agents, for the skin and/or the lips, and in particular the lips.

Needless to say, a person skilled in the art will take care to select the optional additional compounds and/or the amount thereof such that the advantageous properties of the composition used according to the invention are not, or are not substantially, adversely affected by the envisaged addition.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to the skin and/or the lips, for instance water or the oils or organic solvents commonly used in cosmetic compositions. The physiologically acceptable medium (acceptable tolerance, toxicology and feel) is generally adapted to the nature of the support onto which the composition is to be applied, and also to the form in which the composition is to be packaged.

Composition

The composition according to the invention may be more or less liquid and may have the consistency of a gel, preferably of a gel-cream. In particular, it has the consistency of a shear-thinning gel.

Preferably, a composition according to the invention is liquid.

A composition according to the invention preferably has a viscosity of between 50 and 150 poises.

The viscosity of the composition can be measured using a rheometer of the Rheomat RM 200 type from Lamy Rheology with spindle 4 (2 to 23 Pa·s) or spindle 3 at a speed of 200 rpm, at room temperature (25° C.) and under atmospheric pressure (760 mmHg).

A composition according to the invention may in particular be an emulsified gel, the aqueous phase of which constitutes the gelled external phase. As such, a composition according to the invention is different from an emulsion, or from a composition of gel-gel type. Thus, the lipophilic phase is not present in the form of droplets, as in a conventional emulsion.

It is possible to distinguish a composition according to the invention from an emulsion by performing a dilution test.

More specifically, the dilution test consists to put 40 g of product plus 160 g of dilution solvent (water or oil) in a 30 ml plastic beaker. The dilution is performed under controlled agitation to avoid any phenomenon of emulsification. In particular, it is done using a planetary mixer: Speed Mixer™ DAC400FVZ. The Speed Mixer is set to 1500 rpm for 4 minutes. Finally, observation of resulting sample is made with a light microscope at a magnification of ×100 (×10×10). It may be noticed that oils like Parleam® and Xiameter PMX-200 Silicone Fluid 5CS® from Dow Corning are convenient as dilution solvents. In the case of the composition according to the invention, when diluted either in oil or water, a heterogeneous aspect is always observed. When the composition according to the invention is diluted with water, one will observe lumps of oily gel in suspension and when it is diluted with oil, one will observe lumps of aqueous gel in suspension.

On the contrary, upon dilution, emulsions display a different behavior. An O/W emulsion when it is diluted with an aqueous solvent, will gradually thin up without presenting a heterogeneous and lumpy aspect. This same O/W emulsion when diluted with oil, will present a heterogeneous appearance (lumps of O/W emulsion suspended in oil). A W/O emulsion when diluted with an aqueous solvent, will present a heterogeneous appearance (lumps of W/O emulsion is suspended in the water). This same W/O emulsion when diluted with oil, will gradually thin up without presenting a heterogeneous and lumpy aspect.

It is also possible to distinguish an emulsified gel from an emulsion by microscopy, for example with a confocal laser scanning microscope test.

In particular, the aqueous and lipophilic phases of a composition according to the invention are present in an aqueous phase/lipophilic phase ratio of between 40/60 and 90/10, in particular between 45/55 and 85/15, and preferably between 50/50 and 80/20.

Preparation of the Compositions According to the Invention

The compositions according to the invention may be manufactured via the known processes, generally used in the cosmetics or dermatology field.

The compositions may be prepared at room temperature (25° C.) or at high temperature.

For example, the aqueous and oily phases may be prepared beforehand separately, then mixed together before introducing the pulverulent compounds.

Use and Process

A composition according to the invention may more particularly be a composition for making up and/or caring for the skin and/or the lips, in particular the lips.

Preferably, the composition according to the invention is a cosmetic composition for making up the lips.

A composition according to the invention may constitute a liquid lipstick for the lips, a body makeup product, a facial or body care product or an antisun product.

A composition of the invention is in particular a composition intended to be applied to a keratin material, in particular the lips, such as for example a lipstick, a lip balm, a lip gloss or a lip pencil.

Preferably, a composition according to the invention is a lipstick, a lip balm or a lip gloss.

As illustrations of liquid formulations, mention may notably be made of lip glosses or lip inks.

The composition according to the invention can be applied preferably using an applicator, in particular a dip applicator, for example using a flocked dip applicator.

According to another of its aspects, the present invention relates to a cosmetic process for making up and/or caring for keratin materials, in particular the lips, comprising at least one step of applying a composition as defined above to said keratin materials, in particular to said lips.

In particular, the process is a cosmetic process for making up and/or caring for the lips, comprising at least one step of applying a composition as defined above to said lips.

Preferably, the process is a cosmetic process for making up the lips, comprising at least one step of applying a composition as defined above to said lips.

Throughout the description, including the claims, the expression "comprising a" should be understood as being synonymous with "comprising at least one", unless otherwise specified. The terms "between . . . and . . . ", "comprises from . . . to . . . ", "formed from . . . to . . . " and "ranging from . . . to . . . " should be understood as being inclusive of the limits, unless otherwise specified.

The invention is illustrated in greater detail by the examples presented below. Unless otherwise indicated, the amounts shown are expressed as mass percentages.

EXAMPLE

Measurement and Evaluation Methods

Each of the compositions is applied to the lips so as to form a deposit of uniform thickness. The ease of application and also the appearance of the deposit are evaluated (satin, enveloping, smooth effects, homogeneity, freshness, thickness of the deposit, etc.).

Evaluation of the Stability

The stability of the compositions is evaluated by placing the compositions obtained for 1 week, and up to 2 months, at room temperature (25° C.). It can also be evaluated by placing the compositions obtained for 2 months at 45° C. The observation of phase separation, leaching or change in appearance is verified.

Evaluation of Migration, Gloss and Comfort

Migration, gloss and comfort are evaluated by a panel of qualified people on the basis of semi-quantitative maintenance.

The formulations are applied to the lips of a panel of six individuals with fleshy and light lips.

Gloss is evaluated 3 minutes after application of the formula and then one hour and 30 minutes after application.

Migration and comfort are evaluated one hour and 30 minutes after application.

The gloss of a composition may also be evaluated in vitro according to any protocol known to a person skilled in the art.

Alternatively, the gloss and the migration may be evaluated in vivo by means of a Chromasphere SEI-M-02232-CHRO-0 machine as described in patent application FR 2 829 344.

Evaluation of Tackiness

The tacky appearance of the deposits made with the formulae is also evaluated according to the following protocol: each of the compositions is applied to the lips so as to form a deposit of uniform thickness.

The tacky nature is evaluated during drying of the formula after 2 minutes at room temperature (25° C.). To do this, the tackiness is assessed by the subject by bringing the upper lip and the lower lip together several times.

Evaluation of the Wear Property

The wear property over time of a composition reflects its ability to withstand mechanical or physical stresses, such as rubbing or stretching of the made-up surface. The wear property of a composition can be evaluated using sensory methods as indicated below on a panel of qualified persons applying a composition.

The evaluation of the wear property is carried out one hour and 30 minutes after application of the composition on the lips.

Transfer Evaluation

The transfer is evaluated by a sensory test carried out under the following conditions. The composition is applied to the lips, and left to dry at room temperature (25° C.) for 2 minutes.

The transfer is evaluated firstly by a kiss test on the hand and secondly by make-up removal with a conventional make-up remover.

Viscosity

The viscosity of the formulae can be measured using a rheometer of the Rheomat RM 200 type from Lamy Rheology with spindle 4 (2 to 23 Pa·s) at a speed of 200 rpm, at room temperature (25° C.) and under atmospheric pressure (760 mmHg).

Methodology for the Oscillating Dynamic Rheology Measurements

These are harmonic-regime rheology measurements for measuring the elastic modulus. The measurements are taken using a Haake RS600 type rheometer on a product at rest, at 25° C. with a plate-plate spindle with a diameter of 60 mm and a 2 mm gap.

The harmonic-regime measurements make it possible to characterize the viscoelastic properties of the products. The technique consists in subjecting a material to a stress which varies sinusoidally over time and in measuring the response of the material to this stress. In a range in which the behavior is linear viscoelastic behavior (zone in which the strain is proportional to the stress), the stress ($\tau$) and the strain ($\gamma$) are two sinusoidal functions of time which are written in the following manner:

$$\tau(t) = \tau_0 \sin(\omega t)$$

$$\gamma(t) = \gamma_0 \sin(\omega t + \delta)$$

where:

- $\tau_0$ represents the maximum amplitude of the stress (Pa);
- $\gamma_0$ represents the maximum amplitude of the strain (−);
- $\omega = 2\Pi N$ represents the angular frequency (rad·s$^{-1}$) with N representing the frequency (Hz); and
- $\delta$ represents the phase shift of the stress relative to the strain (rad).

Thus, the two functions have the same angular frequency, but they are phase-shifted by an angle $\delta$. Depending on the phase shift $\delta$ between $\tau(t)$ and $\gamma(t)$, the behavior of the system may be apprehended:

- if $\delta=0$, the material is purely elastic;
- if $\delta=\Pi/2$, the material is purely viscous (Newtonian fluid); and
- if $0<\delta<\Pi/2$, the material is viscoelastic.

In general, the stress and the strain are written in complex form:

$$\tau^*(t) = \tau_0 e^{i\omega t}$$

$$\gamma^*(t) = \gamma_0 e^{(i\omega t+\delta)}$$

A complex stiffness modulus, representing the overall resistance of the material to the strain, whether it is of elastic or viscous origin, is then defined by:

$$G^* = \tau^*/\gamma^* = G' + iG''$$

where:

- G' is the storage modulus or elastic modulus, which characterizes the energy stored and totally restituted during a cycle, $G'=(\tau_0/\gamma_0)\cos\delta$; and
- G" is the loss modulus or viscous modulus, which characterizes the energy dissipated by internal friction during a cycle, $G''=(\tau_0/\gamma_0)\sin\delta$.

The parameter retained is the mean stiffness modulus G* recorded at the plateau measured at a frequency of 1 Hz.

Example I

Lip compositions (1) to (7) according to the invention are prepared as described below with the proportions and compounds indicated in tables 1 and 2.

TABLE 1

| Phase | | | Compounds (INCI name) | Content (% by weight relative to the total weight of the white base) | Content (% by weight relative to the total weight of the composition) |
|---|---|---|---|---|---|
| Phase A | White base | WB1 | Water | qs for 100 | 95 |
| | | | Glycerin | 16.9 | |
| | | | Phenoxyethanol | 0.6 | |
| | | WB2 | Trimethylsiloxyphenyl Dimethicone (Belsil 1000, Wacker) | 6.7 | |
| | | | Polypropylsilsesquioxane (and) Isododecane (Dowsil 680 ID Fluid, Dow Corning) | 7.8 | |
| | | | Silicone elastomer (table 2) | 5 | |
| | | WB3 | Hydroxyethyl Acrylate/ Sodium Acryloyldimethyl Taurate Copolymer (Sepinov EMT 10, Seppic) | 3.4 | |
| | | | Water | | qs for 100 |
| Phase B | | | Red 28 (Sensient) | | 0.04 |
| | | | Red 33 (Sensient) | | 0.1 |
| | | | Yellow 6 (Sun) | | 0.1 |
| Phase C | | | Red 7 (and) isopropyl titanium triisostearate (and) triethoxysilylethyl polydimethylsiloxyethyl dimethicone (Kobo) | | 1.1 |

The silicone elastomers used in compositions (1) to (7) are described in detail in table 2 below:

TABLE 2

| Composition | Silicone elastomer (INCI name) |
|---|---|
| Formula (1) | Triethylhexanoin (and) Vinyl Dimethicone/Lauryl Dimethicone Crosspolymer (KSG 43, Shin Etsu) |
| Formula (2) | Dimethicone (and) Dimethicone/PEG-10/15 Crosspolymer (KSG 210, Shin Etsu) |
| Formula (3) | Dimethicone (and) Dimethicone/Polyglycerin-3 Crosspolymer (KSG 710, Shin Etsu) |
| Formula (4) | Dimethicone (and) Dimethicone/Vinyl Dimethicone Crosspolymer (KSG 16, Shin Etsu) |
| Formula (5) | Dimethicone (and) Dimethicone Crosspolymer (Dowsil EL-9241 DM Silicone Elastomer Blend, Dow) |
| Formula (6) | Dimethicone (and) Dimethicone Crosspolymer (Dowsil EL-9140 DM Silicone Elastomer Blend, Dow) |
| Formula (7) | Dimethicone (and) Dimethicone/Vinyltrimethyl-siloxysilicate Crosspolymer (Belsil REG 1102, Wacker) |

Preparation of the Compositions

The compositions are prepared at room temperature (25° C.).

Prior to the preparation of the compositions, the white bases are prepared.

The compounds of phase WB1 are mixed using a Rayneri blender. Separately, the compounds of phase WB2 are mixed using a Rayneri blender or manually with a spatula. Phase WB2 is incorporated into phase WB1, then the mixture is left stirring using a Rayneri blender for 10 minutes. The compound of phase WB3 is sprinkled into the mixture and the stirring speed is gradually increased as the gel is created. The whole mixture is left stirring for 10 minutes, until complete disappearance of gel clumps.

The white base is mixed with water using a Rayneri blender to form phase A. The compounds of phase B are introduced into phase A by sprinkling them, then the mixture is left under stirring for 10 minutes until complete solubilization of the dyes. The compound of phase C is incorporated into the mixture using a spatula, with stirring using a Rayneri blender. The composition is stirred for 15 minutes, in order to ensure good dispersion of the pigments.

Results

The results obtained with compositions (1) to (7) according to the invention are described in detail below.

Compositions (1) to (7) have a satin finish on the lips. All of the compositions have a good wear property on the lips and transfer little. The deposit is homogeneous and comfortable.

Composition (1) is fresh on application, and does not migrate. Furthermore, the deposit obtained with composition (1) is thin. The white base of composition (1) has a viscosity of 76 poises and the final composition (1) has a viscosity of 124 poises (average over two measurements), according to the measurement protocol described above. Moreover, the color effect obtained with composition (1) is intense.

Composition (2) is very fresh on application, is not tacky and does not migrate.

Composition (3) is very fresh on application, and does not migrate. The film obtained with composition (3) is glossy.

Composition (4) has an enveloping finish, thick at the start then very quickly becomes thinner in feeling on the lips.

The deposit of composition (5) on the lips is not tacky.

Composition (6) does not migrate.

The deposit of composition (7) on the lips is glossy and not tacky.

Composition (7) exhibits little or no tack. Furthermore, the film obtained with composition (7) has an enveloping effect on the lips.

Example II

Lip compositions (1) according to example I, and (8) to (11) are prepared with the proportions and compounds indicated in tables 3 and 4.

TABLE 3

| Phase | | | Compounds (INCI name) | Content (% by weight relative to the total weight of the white base) | Content (% by weight relative to the total weight of the composition) |
|---|---|---|---|---|---|
| Phase A | White base | WB1 | Water | qs for 100 | 95 |
| | | | Glycerin | 16.9 | |
| | | | Phenoxyethanol | 0.6 | |
| | | WB2 | Oil (table 4) | 6.7 | |
| | | | Polypropylsilsesquioxane (and) Isododecane (Dowsil 680 ID Fluid, Dow Corning) | 7.8 | |
| | | | Triethylhexanoin (and) Vinyl Dimethicone/Lauryl Dimethicone Crosspolymer (KSG 43, Shin Etsu) | 5 | |
| | | WB3 | Hydroxyethyl Acrylate/ Sodium Acryloyldimethyl Taurate Copolymer (Sepinov EMT 10, Seppic) | 3.4 | |
| | | | Water | | qs for 100 |
| Phase B | | | Red 28 (Sensient) | | 0.04 |
| | | | Red 33 (Sensient) | | 0.1 |
| | | | Yellow 6 (Sun) | | 0.1 |
| Phase C | | | Red 7 (and) isopropyl titanium triisostearate (and) triethoxysilylethyl polydimethylsiloxyethyl dimethicone (Kobo) | | 1.1 |

The compositions are prepared according to the procedure described in detail in example I.

The oils used in compositions (1), and (9) to (12) are described in detail in table 4 below:

TABLE 4

| Composition | Silicone oil (INCI name) |
|---|---|
| Formula (1) according to the invention | Trimethylsiloxyphenyl Dimethicone (Belsil 1000, Wacker) |
| Formula (8) outside the invention | Phenyl trimethylsiloxy trisiloxane (Dowsil 556 Cosmetic Grade Fluid, Dow Corning) |
| Formula (9) according to the invention | Dimethicone (1000 cst) (Xiameter PMX-200 Silicone Fluid 1000 cst, Dow Corning) |
| Formula (10) outside the invention | Dimethicone (2 cst) (Xiameter PMX-200 Silicone Fluid 2 cst, Dow Corning) |
| Formula (11) outside the invention | Octyldodecanol (Eutanol G, BASF) |

Results

The results obtained with compositions (1) and (8) to (11) are described in detail below. Compositions (1) and (9) according to the invention have a satin finish on the lips, transfer little and do not migrate. The deposit is homogeneous and comfortable.

Composition (1) is fresh on application. Furthermore, the deposit obtained with composition (1) is thin and has a good wear property.

Composition (9) leaves a glossy film on the lips.

Compositions (8), (10) and (11) outside the invention are not stable.

Furthermore, compositions (8) and (11) outside the invention stain the teeth and have a significant transfer. The deposit obtained with composition (10) outside the invention is not homogeneous. The deposit obtained with composition (11) outside the invention is thick and inhomogeneous. Composition (11) migrates.

Example III

Lip compositions (1) according to example I, and (12) according to the invention are prepared with the proportions and compounds indicated in table 5.

TABLE 5

| Phase | | | Compounds (INCI name) | Content (% by weight relative to the total weight of the white base) Formula (1) | Formula (12) | Content (% by weight relative to the total weight of the composition) |
|---|---|---|---|---|---|---|
| Phase A | White Base | WB1 | Water | qs for 100 | qs for 100 | 95 |
| | | | Glycerin | 16.9 | 16.9 | |
| | | | Phenoxyethanol | 0.6 | 0.6 | |
| | | WB2 | Trimethylsiloxyphenyl Dimethicone (Belsil PDM 1000, Wacker) | 6.7 | 6.7 | |
| | | | Polypropylsilsesquioxane (and) Isododecane (Dowsil 680 ID Fluid, Dow Corning) | 7.8 | 7.8 | |
| | | | Triethylhexanoin (and) Vinyl Dimethicone/Lauryl Dimethicone Crosspolymer (KSG 43, Shin Etsu) | 5 | 5 | |
| | | WB3 | Hydroxyethyl Acrylate/Sodium Acryloyldimethyl Taurate | 3.4 | / | |

TABLE 5-continued

| Phase | Compounds (INCI name) | Content (% by weight relative to the total weight of the white base) Formula (1) | Formula (12) | Content (% by weight relative to the total weight of the composition) |
|---|---|---|---|---|
| | Copolymer (Sepinov EMT 10, Seppic) | | | |
| | Ammonium Polyacryloyldimethyl Taurate (Hostacerin AMPS, Clariant) | / | 3.4 | |
| | Water | | | qs for 100 |
| Phase B | Red 28 (Sensient) | | | 0.04 |
| | Red 33 (Sensient) | | | 0.1 |
| | Yellow 6 (Sun) | | | 0.1 |
| Phase C | Red 7 (and) isopropyl titanium triisostearate (and) triethoxysilylethyl polydimethylsiloxyethyl dimethicone (Kobo) | | | 1.1 |

The compositions are prepared according to the procedure described in detail in example I.

Results

The results obtained with compositions (1) and (12) are described in detail below. Compositions (1) and (12) according to the invention have a satin finish on the lips, and transfer little or not at all. Furthermore, they also migrate little or not at all. The deposit is homogeneous and comfortable.

Example IV

Lip compositions (13) to (16) according to the invention are prepared as described below with the proportions and compounds indicated in table 6. The contents are weight percentages relative to the total weight of the composition.

TABLE 6

| Compounds (INCI name) | Formula (13) Content | Formula (14) Content | Formula (15) Content | Formula (16) Content |
|---|---|---|---|---|
| Water | qs for 100 | qs for 100 | qs for 100 | qs for 100 |
| Glycerin | 16 | 16 | 16 | 16 |
| Phenoxyethanol | 0.5 | 0.5 | 0.5 | 0.5 |
| Hydroxyethyl Acrylate/Sodium Acryloyldimethyl Taurate Copolymer (Sepinov EMT 10, Seppic) | 3.2 | 3.2 | 3.2 | 3.2 |
| Triethylhexanoin (and) Vinyl Dimethicone/Lauryl Dimethicone Crosspolymer (KSG 43, Shin Etsu) | 6.7 | 2.3 | 9.3 | 2.3 |
| Dimethicone (and) Trimethylsiloxysilicate (Dowsil 593 Fluid, Dow Corning) | / | 7.5 | 2.5 | 7.5 |
| Trimethylsiloxysilicate (and) Polypropylsilsesquioxane (Dow Corning MQ-1640 Flake Resin, Dow Corning) | / | 5.2 | / | 5.2 |
| Polymethylsilsesquioxane (Belsil PMS MK Powder Silicone Resin, Wacker) | / | 0.3 | 1.7 | / |
| Trimethylsiloxysilicate (Silsoft 74, Momentive Performance Materials) | 7.4 | / | / | / |
| Trimethylsiloxyphenyl Dimethicone (Belsil PDM 1000, Wacker) | / | 5.8 | 2.8 | 5.8 |
| Tridecyl Trimellitate (Liponate TDTM, Vantage Specialty Chemicals) | 6.4 | / | / | / |
| Isododecane | / | 2.1 | 0.7 | 2 |
| Red 33 (Sensient) | 0.1 | 0.1 | 0.1 | 0.1 |
| Red 28 (Sensient) | 0.04 | 0.04 | 0.04 | 0.04 |
| Yellow 6 (Sun) | 0.1 | 0.1 | 0.1 | 0.1 |
| Red 7 (and) isopropyl titanium triisostearate (and) triethoxysilylethyl polydimethylsiloxyethyl dimethicone (Kobo) | 1.4 | 1.1 | 1.1 | 11 |

Preparation of the Compositions

Prior to the preparation of the compositions, when they contain them, a premix is produced with trimethylsiloxysilicate (and) polypropylsilsesquioxane and isododecane. The preparation is carried out on 300 g with a resin/solvent ratio of 72/28. The isododecane is heated to 75° C., and the trimethylsiloxysilicate (and) polypropylsilsesquioxane is sprinkled little by little with stirring using a Rayneri blender, until complete dissolution in order to prevent gel clumps. A transparent thickened liquid is obtained, poured into a pot and then left to cool for use when it is cold.

Likewise, prior to the preparation of the compositions, when they contain them, a premix is produced with polymethylsilsesquioxane and isododecane. The preparation is carried out on 300 g with a resin/solvent ratio of 72/28. The isododecane is heated to 40° C., and the polymethylsilsesquioxane is sprinkled little by little with stirring using a Rayneri blender. A thickened liquid is obtained, then left to cool for use when it is cold.

The compositions are prepared at room temperature (25° C.).

The aqueous phase is prepared using a Rayneri blender by mixing water, glycerin and phenoxyethanol.

Separately, the fatty phase is prepared by mixing using a Rayneri blender, or by mixing manually with a spatula, the resins, elastomers and oils. For formula (14), the elastomer and the resin are premixed, then the oil is added.

The fatty phase is incorporated into the aqueous phase and the mixture is left stirring using a Rayneri blender for 10 minutes.

The hydroxyethyl acrylate/sodium acryloyldimethyl taurate copolymer is then sprinkled into the mixture and the stirring speed is gradually increased as the gel is created. The whole mixture is left stirring for 10 minutes, until complete disappearance of gel clumps.

The dyes are then introduced, and left to dissolve with stirring for 10 minutes. The pigments are introduced by sprinkling them, then the mixture is left stirring for 10-15 minutes.

The viscosity of compositions (13) to (16) was measured according to the protocol described above. The results are described in detail in table 7 below (average over two measurements).

TABLE 7

| | Composition | | | |
|---|---|---|---|---|
| | Formula (13) | Formula (14) | Formula (15) | Formula (16) |
| Viscosity | 116 Poises | 80 Poises | 123 Poises | 78 Poises |

Results

The results obtained with compositions (13) to (16) according to the invention are described in detail below.

Compositions (13) to (16) have a satin finish on the lips, and transfer little or not at all. Furthermore, the deposits obtained with compositions (13) to (16) are thin, homogeneous and comfortable and have a good wear property. They do not stain teeth, or stain teeth very little, after drying.

Compositions (13), (14) and (16) are also fresh on application and do not migrate.

The deposits of compositions (14), (15) and (16) on the lips are not, or not very, tacky.

Example V

Lip compositions (1) according to example I, and (17) to (20) according to the invention are prepared as described below with the proportions and compounds indicated in table 8.

TABLE 8

| Phase | | | (Compounds INCI name) | Content (% by weight relative to the total weight of the white base) Formula (1) | Formula (17) | Formula (18) | Formula (19) | Formula (20) | Content (% by weight relative to the total weight of the composition) |
|---|---|---|---|---|---|---|---|---|---|
| Phase A | White Base | WB1 | Water | qs for 100 | qs for 100 | qs for 100 | qs for 100 | qs for 100 | 95 |
| | | | Glycerin | 16.9 | / | 5 | 10 | 15 | |
| | | | Phenoxyethanol | 0.6 | 0.6 | 0.6 | 0.6 | 0.6 | |
| | | WB2 | Trimethylsiloxyphenyl Dimethicone (Belsil PDM 1000, Wacker) | 6.7 | 6.7 | 6.7 | 6.7 | 6.7 | |
| | | | Polypropylsilsesquioxane (and) Isododecane (Dowsil 680 ID Fluid, Dow Corning) | 7.8 | 7.8 | 7.8 | 7.8 | 7.8 | |
| | | | Triethylhexanoin (and) Vinyl Dimethicone/ Lauryl Dimethicone Crosspolymer (KSG 43, Shin Etsu) | 5 | 5 | 5 | 5 | 5 | |
| | | WB3 | Hydroxyethyl Acrylate/Sodium Acryloyldimethyl Taurate Copolymer (Sepinov EMT 10, Seppic) | 3.4 | 3.4 | 3.4 | 3.4 | 3.4 | |
| | | | Water | | | | | | qs for 100 |
| Phase B | | | Red 28 (Sewsient) | | | | | | 0.04 |
| | | | Red 33 (Sensient) | | | | | | 0.1 |
| | | | Yellow 6 (Sun) | | | | | | 0.1 |
| Phase C | | | Red 7 (and) isopropyl titanium triisostearate (and) triethoxysilylethyl polydimethylsiloxyethyl dimethicone (Kobo) | | | | | | 1.1 |

The compositions are prepared according to the procedure described in detail in example I.

Results

The results obtained with compositions (1) and (17) to (20) are described in detail below. All of the compositions have a satin finish on the lips. The deposit is homogeneous. They have a good wear property on the lips and transfer little. They are fresh on application, and do not migrate. They do not stain teeth after drying.

Furthermore, the deposits obtained with compositions (1) and (20) are thin and very comfortable. Moreover, the color effect obtained with these compositions is intense.

Example VI

Lip compositions (21) according to the invention and (22) to (28) outside the invention are prepared as described below with the proportions and compounds indicated in table 9.

TABLE 9

| Phase | | | Compounds (INCI name) | Content (% by weight relative to the total weight of the white base) Formula (21) according to the invention | Formula (22) according to the invention | Formula (23) according to the invention | Formula (24) according to the invention |
|---|---|---|---|---|---|---|---|
| Phase A | White Base | WB1 | Water | qs for 100 | qs for 100 | qs for 100 | qs for 100 |
| | | | Glycerin | 16.9 | 16.9 | 16.9 | 16.9 |
| | | | Phenoxyethanol | 0.6 | 0.6 | 0.6 | 0.6 |
| | | WB2 | Trimethylsiloxyphenyl Dimenthicone (Belsil PDM 1000, Wacker) | 6.7 | 11.4 | / | 67 |
| | | | Polypropylsilsesquioxane (and) Isododecane (Dowsil 680 ID Fluid, Dow Corning) | 7.8 | 13.2 | 10.7 | 7.8 |
| | | | Triethylhexanoin (and) Vinyl Dimethicone/Lauryl Crosspolymer (KSG 43, Shin Etsu) | 101 | / | 13.9 | / |
| | | WB3 | Hydroxyethyl Acrylate/ Sodium Acryloyldimethyl Taurate Copolymer (Sepinov EMT 10, Seppic) | 3.4 | 3.4 | 3.4 | 5.4 |
| | | | Water | | | | |
| Phase B | | | Red 28 (Sensient) | | | | |
| Phase C | | | Red 7 (and) isopropyl titanium triisostearate (and) triethoxysilylethyl polydimethylsiloxyethyl dimethicone (Kobo) | | | | |

| Phase | | | Content (% by weight relative to the total weight of the white base) Formula (25) according to the invention | Formula (26) according to the invention | Formula (27) according to the invention | Formula (28) according to the invention | Content (% by weight relative to the total weight of the composition) |
|---|---|---|---|---|---|---|---|
| Phase A | White Base | WB1 | qs for 100 | qs for 100 | qs for 100 | qs for 100 | 95 |
| | | | 16.9 | 16.9 | 16.9 | 16.9 | |
| | | | 0.6 | 0.6 | 0.6 | 0.6 | |
| | | WB2 | / | / | / | 6 | |
| | | | 7.8 | 24.7 | 7.8 | / | |
| | | | 10.1 | / | / | 10.1 | |
| | | WB3 | 3.4 | 3.4 | 3.4 | 3.4 | |
| | | | Water | | | | qs for 100 |
| Phase B | | | Red 28 (Sensient) | | | | 0.2 |
| Phase C | | | Red 7 (and) isopropyl titanium triisostearate (and) triethoxysilylethyl polydimethylsiloxyethyl dimethicone (Kobo) | | | | 1.1 |

The compositions are prepared according to the procedure described in detail in example I.

Results

The results obtained with compositions (21) to (28) are described in detail below.

Composition (21) according to the invention has a smooth and satin finish and also a good wear property on the lips. The deposit is homogeneous, is not tacky and transfers little. It is fresh on application, and does not migrate. Furthermore, the deposit obtained with composition (21) is thin and very comfortable.

The deposits obtained with compositions (22), (24), (25), (26), (27) and (28) outside the invention are tacky, or even very tacky.

Furthermore, compositions (23), (24) and (28) outside the invention stain the teeth. Compositions (22), (23), (25), (26) and (28) transfer a lot.

Composition (22) outside the invention is runny, and the deposit is not homogeneous during drying. The deposit transfers a lot and leaves pieces of film.

Composition (23) leads to leaching on the lips.

The deposit of composition (24) is not comfortable, the film sets rapidly. It tugs at the corners of the lips.

Compositions (25) and (28) are not homogeneous, they leave pieces on the lips. Furthermore, the color effect is not intense.

The invention claimed is:

1. A composition, comprising:

an aqueous phase comprising water in a content of between 40% and 80% by weight relative to a total weight of the composition, and containing at least one non-particulate synthetic polymeric gelling agent;

an oily phase containing:

(i) a silicone elastomer;

(ii) a silicone resin; and (iii) from 1% to 12% by weight relative to the total weight of the composition, of a nonvolatile oil selected from the group consisting of a non-volatile silicone oil comprising at least one dimethicone group selected from non volatile phenyl silicone oils comprising at least one dimethicone group, tridecyl trimellitate and mixtures thereof, wherein the composition is in a form different from an emulsion and different from a composition of gel-gel.

2. The composition as claimed in claim 1, wherein the at least one non-particulate synthetic polymeric gelling agent is selected from the group consisting of associative polymers, polyacrylamides, crosslinked and/or neutralized 2-acrylamido-2-methylpropanesulfonic acid polymers and copolymers, modified or unmodified carboxyvinyl polymers, and mixtures thereof.

3. The composition as claimed in claim 1, wherein a content of the at least one non-particulate gelling agent is from 0.1% to 6% by weight of non-particulate synthetic polymeric gelling agent(s), relative to the total weight of the composition.

4. The composition as claimed in claim 1, wherein the silicone elastomer is selected from the group consisting of Vinyl Dimethicone/Lauryl Dimethicone Crosspolymer, Dimethicone/PEG-10/15 Crosspolymer, Dimethicone/Polyglycerin-3 Crosspolymer, Dimethicone/Vinyl Dimethicone Crosspolymer, Dimethicone Crosspolymer, Dimethicone/Vinyltrimethylsiloxysilicate Crosspolymer, and their mixtures.

5. The composition as claimed in claim 1, wherein the silicone elastomer is selected from the group consisting of Triethylhexanoin and Vinyl Dimethicone/Lauryl Dimethicone Crosspolymer, Dimethicone and Dimethicone/PEG-10/15 Crosspolymer, Dimethicone and Dimethicone/Polyglycerin-3 Crosspolymer, Dimethicone and Dimethicone/Vinyl Dimethicone Crosspolymer, Dimethicone and Dimethicone Crosspolymer, Dimethicone Crosspolymer and Dimethicone and Dimethicone/Vinyltrimethylsiloxysilicate Crosspolymer.

6. The composition as claimed in claim 1, comprising from 0.2% to 20% by weight of the silicone elastomer, relative to the total weight of the composition.

7. The composition as claimed in claim 1, wherein the silicone resin is selected from the group consisting of silicone resins of MQ, T and MQT.

8. The composition as claimed in claim 1, wherein the silicone resin is selected from the group consisting of Polypropylsilsesquioxane and Isododecane, Dimethicone and Trimethylsiloxysilicate, Trimethylsiloxysilicate and Polypropylsilsesquioxane, Polymethylsilsesquioxane and Trimethylsiloxysilicate.

9. The composition as claimed in claim 1, comprising from 0.5% to 20% by weight of the silicone resin, relative to the total weight of the composition.

10. The composition as claimed in claim 1, wherein the non-volatile phenyl silicone oil comprising at least one dimethicone group is present and has a viscosity at 25° C. of greater than or equal to 9 centistokes (cSt), measured according to the ASTM D-445 standard.

11. The composition as claimed in claim 1, comprising at least one non-volatile phenyl silicone oil comprising at least one dimethicone group.

12. The composition as claimed in claim 1, wherein the nonvolatile oil is tridecyl trimellitate.

13. The composition as claimed in claim 1, further comprising at least one polyol.

14. The composition as claimed in claim 13, wherein a content of the at least one polyol is from 1% to 22% by weight relative to the total weight of the composition.

15. The composition as claimed in claim 1, further comprising at least one colorant.

16. The composition as claimed in claim 15, wherein a content of the at least one colorant is from 0.1% to 10% by weight relative to the total weight of the composition.

17. The composition as claimed in claim 1, which is in the form of a gel.

18. A cosmetic process for making-up the lips, comprising applying the composition as claimed in claim 1, to the lips.

19. A cosmetic process for making up and/or caring for keratin materials, comprising applying a composition as claimed in claim 1 to said keratin materials.

* * * * *